US012678771B1

(12) United States Patent
Nasiruzzaman Shaikh et al.

(10) Patent No.: US 12,678,771 B1
(45) **Date of Patent: *Jul. 14, 2026**

(54) CARBON DIOXIDE HYDROGENATION CATALYST

(71) Applicant: KING FAHD UNIVERSITY OF PETROLEUM AND MINERALS, Dhahran (SA)

(72) Inventors: M. Nasiruzzaman Shaikh, Dhahran (SA); Mahbuba Aktary, Dhahran (SA); Atif Alzahrani, Dhahran (SA); Mohamed Ahmed Yahya Sanhoob, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 19/189,081

(22) Filed: Apr. 24, 2025

(30) Foreign Application Priority Data

Apr. 17, 2025 (SA) ................................ 1020252502

(51) Int. Cl.

| | |
|---|---|
| ***B01J 23/04*** | (2006.01) |
| ***B01J 21/04*** | (2006.01) |
| ***B01J 21/16*** | (2006.01) |
| ***B01J 23/745*** | (2006.01) |
| ***B01J 35/40*** | (2024.01) |
| ***B01J 35/61*** | (2024.01) |

(Continued)

(52) U.S. Cl.

CPC ............... *B01J 23/04* (2013.01); *B01J 21/04* (2013.01); *B01J 21/16* (2013.01); *B01J 23/745* (2013.01);

(Continued)

(58) Field of Classification Search

CPC ........ B01J 23/04; B01J 35/613; B01J 35/633; B01J 35/40; B01J 21/04; B01J 21/16;

(Continued)

(56) References Cited

U.S. PATENT DOCUMENTS

| | | | |
|---|---|---|---|
| 10,537,872 | B1 | 1/2020 | Saha |
| 2021/0229073 | A1 | 7/2021 | Alsolami et al. |
| 2021/0268480 | A1 | 9/2021 | Alsolami et al. |

FOREIGN PATENT DOCUMENTS

| | | | |
|---|---|---|---|
| CN | 116410075 | A | 7/2023 |
| CN | 117282444 | A | 12/2023 |

OTHER PUBLICATIONS

J. Sustain. Metall. Feb. 2016, 316-331 (Evans) (Year: 2016).*

(Continued)

*Primary Examiner* — Amy C Bonaparte
*Assistant Examiner* — Derek Rhoades
(74) *Attorney, Agent, or Firm* — Oblon, McClelland, Maier & Neustadt, L.L.P.

(57) ABSTRACT

A carbon dioxide ($CO_2$) hydrogenation catalyst and a method of its preparation. The $CO_2$ hydrogenation catalyst includes an alkali-metal enriched bauxite residue including calcium carbonate ($CaCO_3$), iron(III) oxide ($Fe_2O_3$), iron (III) oxyhydroxide (FeO(OH)), aluminum hydroxide ($Al(OH)_3$), sodalite, muscovite, and $Na_5Al_2CSi_3O_{15}$. The $CO_2$ hydrogenation catalyst further includes 1 weight percent (wt. %) to 10 wt. % potassium based on a total weight of the $CO_2$ hydrogenation catalyst by inductively coupled plasma optical emission spectroscopy (ICP-OES). The $CO_2$ hydrogenation catalyst is used in a method of hydrogenating carbon dioxide to produce olefins.

13 Claims, 15 Drawing Sheets

(51) Int. Cl.
*B01J 35/63* (2024.01)
*B01J 37/00* (2006.01)
*B01J 37/08* (2006.01)
*B01J 37/18* (2006.01)
*C07C 1/04* (2006.01)

(52) U.S. Cl.
CPC ............ *B01J 35/40* (2024.01); *B01J 35/613* (2024.01); *B01J 35/633* (2024.01); *B01J 37/0036* (2013.01); *B01J 37/08* (2013.01); *B01J 37/18* (2013.01); *C07C 1/044* (2013.01)

(58) Field of Classification Search
CPC ...... B01J 23/745; B01J 37/0036; B01J 37/08; B01J 37/18; C07C 1/044
See application file for complete search history.

(56) References Cited

OTHER PUBLICATIONS

Sci. Total Environ. 2018, 622-623, 849-860 (Bolanz et al.) (Year: 2018).*
J. Eur. Ceram. Soc. 2000, 20, 235-244 (Sglavo et al.) (Year: 2000).*
Appl. Catal. B: Environ. 2019, 241, 430-441 (Weber et. al.) (Year: 2019).*
Fuel Process. Technol. 2022, 233, 107316, pp. 1-12 (Wang et al.) (Year: 2022).*
Energ. Source Part A 2024, 46 13522-13535 (Qi et al.) (Year: 2024).*
Ind. Eng. Chem. Res. 2019, 58, 15803-15817 (Das et al.) (Year: 2019).*
Chem. Asian J. 2024, 19, e202301007, pp. 1-26 (Aktary et al.) (Year: 2024).*
J. Environ. Manag. 2018, 210, 210-225 (McGladdery et al.) (Year: 2018).*
Water Sci. Technol. 2022, 86, 2106-2123 (Chen et al.) (Year: 2022).*
Artem Russkikh, et al., "Turning Waste into Value: Potassium-Promoted Red Mud as an Effective Catalyst for the Hydrogenation of CO2", ChemSusChem, vol. 13, Issue 11, Apr. 28, 2020, pp. 2981-2987.
Huirong Zhao, et al., "Chemical looping conversion of CO2 based on bauxite residue: Thermodynamic behavior and kinetic characteristics", Journal of the Energy Institute, vol. 109, Aug. 2023, 101300, 5 pages.

* cited by examiner

CARBON DIOXIDE HYDROGENATION CATALYST

CROSS-REFERENCE TO RELATED APPLICATION

The present disclosure claims the benefit of Saudi Patent Application No. 1020252502, filed on Apr. 17, 2025 with the Saudi Authority for Intellectual Property Office, which is incorporated herein by reference in its entirety.

STATEMENT OF PRIOR DISCLOSURE BY AN INVENTOR

Aspects of the present disclosure are described in Mahbuba Aktary, et. al., "Utilizing red mud from industrial waste as catalysts for the hydrogenation of $CO_2$ into value added chemicals", RSC Adv., 2025, 15, 4970-4986, which is incorporated herein by reference in its entirety.

STATEMENT OF ACKNOWLEDGEMENT

The authors would like to acknowledge the support provided by the National Industrial Development and Logistic Program of Saudi Arabia through the Renewable Energy Technical Incubator (RETI) at King Fahd University of Petroleum & Minerals (KFUPM), Dhahran, Saudi Arabia, under Grant No. CREP2522 for this work.

BACKGROUND

Technical Field

The present disclosure is directed towards a carbon dioxide ($CO_2$) hydrogenation reaction, and more particularly, relates a $CO_2$ hydrogenation catalyst and a method of production thereof.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Rising levels of $CO_2$, primarily driven by human activities such as fossil fuel burning, industrial processes, and deforestation, are contributing to global climate change [Nunes, L. J. R., Environments, 10, 66, 2023]. The changing climate has many adverse effects, including rising temperatures, extreme weather events, and rising sea levels. Numerous initiatives have been made to prevent catastrophic environmental disasters due to greenhouse gas emissions, including the implementation of technologies and policies to mitigate the negative consequences of using fossil fuels [Kuramochi, T. et al., Climate Policy, 20, 275-291, 2020; Brdulak, A., et. al., Energies (Basel), 13, 4239, 2020; and Gilligan, J. M. & Vandenbergh, M. P., Energy Res Soc Sci, 60, 101400, 2020]. In order to mitigate high $CO_2$ levels, carbon capture, utilization, and storage (CCUS) technologies have become vital mitigation strategies for the sustainable development of nations [Xiaoping, Z., et. al., Ecological Chemistry and Engineering S, 21, 617-622, 2015]. In particular, a workable solution to urgent problem may be capturing atmospheric $CO_2$ and converting the $CO_2$ to useful chemical products. Various conversion paradigms have been investigated, including photoreduction, electroreduction, photo-chemical methods, thermochemical methods, electrochemical method, or biological methods into value-added products. Among these, thermochemical processes are preferred for $CO_2$ conversion in a plurality of industrial application due to the process flexibility, scalability, and economic-environmental advantages.

Catalytic hydrogenation is an attractive thermochemical method for converting $CO_2$ into various high-value-added products, including CO, $CH_4$, methanol, dimethyl ether, and olefins. For example, a bimetallic 40CuCe(rod) catalyst showed 36.5% to 41.1% conversion with 100% CO selectivity at 400° C. [L u, B. et al., Fuel, 276, 118135, 2020]. In another example, 2.5 wt. % nickel (Ni) and 2.5 wt. % cobalt (Co) supported on $ZrO_2/Al_2O_3$ catalysts yielded 83.8% $CO_2$ conversion with 73.7% $CH_4$ selectivity [Al-Fatesh, A. et. al., Int J Hydrogen Energy 43, 12069-12080 (2018).]. Other examples of catalytic systems for $CO_2$ hydrogenation to ethanol include $Zr_{12}$-bpdc-CuCs, $Pd_2$CuNPs/P25, $CoMoC_x$, Cu@Na-Beta, Au/a-$TiO_2$ [An, B. et al., Nat Catal, 2, 709-717, 2019; Bai, S. et al., J A m C hem Soc, 139, 6827-6830, 2017; Zhang, H., et. al., Chem Cat Chem, 13, 3333-3339, 2021; Ding, L. et al., Chem, 6, 2673-2689, 2020; and Wang, D. et al., Chemical Communications, 52, 14226-14229, 2016].

However, the production of olefins from $CO_2$ presents different challenges compared to CO or ethanol. Olefins are attractive target chemicals as olefins are the primary raw material used in the industrial manufacturing of diverse products such as plastics, polymers, detergents, and lubricants. Specifically, ethylene ($C_2$) is widely employed as a precursor in synthesizing thermoplastic oligomers or polymers. Several low-cost metal-based catalysts, such as $Fe_2O_3$-CT600, Fe—Co(0.17)/K (1.0)/$Al_2O_3$, ZnZrO/SAPO-34, and Na—$Fe_3O_4$/HZSM-5, have been evaluated and found to be favorable for $CO_2$ hydrogenation for the production of $C_{2+}$ hydrocarbons through the modified Fischer-Tropsch (FT) process [Li, W. et. al., RSC Adv, 8, 7651-7669, 2018]. However, comparatively little work has been dedicated to converting $CO_2$ to lower olefins compared to other target chemicals.

In an example, Fe—Co—K/$Al_2O_3$-400 catalysts showed 49% $CO_2$ conversion and 37% olefins selectivity at 340° C. [Numpilai, T., et. al., Appl Catal A Gen, 547, 219-229, 2017]. The addition of Zr with K—Fe catalyst enhanced conversion (above 54%) as well as olefins selectivity was above 53% at 320° C. and 2 M Pa. The catalysts K—FeX (X=15, 30, 60), a bulk Fe catalyst with a large surface area that was promoted by K, was shown to have more activity than materials based on commercial $Fe_3O_4$ and α-$Fe_2O_3$ [Visconti, C. G., et al., Appl Catal B, 200, 530-542, 2017].

The catalyst support may play a major role on the metal-support interaction and is essential in spreading the active metal [Van Deelen, T. W., et. al., Nat Catal, 2, 955-970, 2019]. Catalytic activity may be influenced by factors like metal immobilization, chemical states, and crystallographic orientation. Supports such as metal oxides, clays, zeolites, and MOFs have been explored, with inorganic metal oxides offering superior chemical, mechanical, and thermal stability.

These conventional $CO_2$ hydrogenation materials show promise but suffer from disadvantages including high costs, limited selectivity, short lifetime due to facile catalyst deactivation, their own environmental concerns with production and use of the catalysts themselves, and high energy demands. Further, many of these catalysts also face scalability challenges and lack integration with existing industrial setups. Addressing these drawbacks is crucial for developing cost-effective, sustainable, and efficient catalytic systems.

Accordingly, one object of the present disclosure is to provide a $CO_2$ hydrogenation catalyst and a method of production thereof that may circumvent the drawbacks and limitations, such as low scalability, high cost, and low efficiency, of materials known in the art.

SUMMARY

According to a first aspect, the present disclosure relates to a carbon dioxide ($CO_2$) hydrogenation catalyst. In some embodiments, the $CO_2$ hydrogenation catalyst includes an alkali-metal enriched bauxite residue including calcium carbonate ($CaCO_3$), iron(III) oxide ($Fe_2O_3$), iron(III) oxyhydroxide ($FeO(OH)$), aluminum hydroxide($Al(OH)_3$), sodalite, muscovite, and $Na_5Al_2CSi_3O_{15}$. In some embodiments, the $CO_2$ hydrogenation catalyst further includes 1 weight percent (wt %) to 10 wt % potassium based on a total weight of the $CO_2$ hydrogenation catalyst by inductively coupled plasma optical emission spectroscopy (ICP-OES).

In some embodiments, the $CO_2$ hydrogenation catalyst further includes aluminum oxide ($Al_2O_3$) and titanium dioxide ($TiO_2$).

In some embodiments, the $CO_2$ hydrogenation catalyst further includes aluminum oxyhydroxide ($AlO(OH)$).

In some embodiments, the $TiO_2$ is rutile and the $Fe_2O_3$ is $\alpha$-$Fe_2O_3$.

In some embodiments, the catalyst includes 2.5 wt % to 5 wt % potassium based on the total weight of $CO_2$ hydrogenation catalyst by ICP-OES.

In some embodiments, the catalyst has a hydrogen temperature-programmed reduction ($H_2$-TPR) of 400 micromoles per gram (μmol/g) to 600 μmol/g at a temperature of 200° C. to 850° C.

In some embodiments, the catalyst has a surface area of 10 square meters per gram ($m^2/g$) to 20 $m^2/g$ and a pore volume of 0.015 cubic centimeters per gram ($cm^3/g$) to 0.030 $cm^3/g$.

In some embodiments, the catalyst has a mean particle size of 0.1 micrometer (μm) to 10 μm.

The present disclosure also relates to a method of forming the $CO_2$ hydrogenation catalyst. In some embodiments, the method includes calcining red mud at 300° C. to 700° C. for 1 hour (h) to 12 h to produce a calcined red mud (RM). In some embodiments, the method further includes treating the calcined red mud with a concentrated acid to produce an acid-treated red mud, grinding the acid-treated red mud with a potassium source to form a precursor mixture, and calcining the precursor mixture at 300° C. to 700° C. for 1 h to 12 h to produce the $CO_2$ hydrogenation catalyst.

In some embodiments, the potassium source includes potassium nitrate ($KNO_3$).

In some embodiments, the potassium source is substantially free of potassium hydroxide (KOH).

In some embodiments, the concentrated acid is hydrochloric acid (HCl) having a concentration of 30% to 38% by weight in water.

The present disclosure also relates to a method of hydrogenating carbon dioxide. In some embodiments, the method includes introducing a gaseous mixture of $CO_2$ and hydrogen ($H_2$) into a reactor including particles of the $CO_2$ hydrogenation catalyst and reacting at least a portion of the $CO_2$ and $H_2$ in the gaseous mixture in the presence of the red mud catalyst at a temperature of 200° C. to 550° C. to form a hydrocarbon mixture including an olefin having 2 to 4 carbon atoms.

In some embodiments, the gaseous mixture has a volume ratio of the $CO_2$ to the $H_2$ of 1:10 to 10:1.

In some embodiments, the gaseous mixture has a volume ratio of the $CO_2$ to the $H_2$ of 1:1 to 5:1.

In some embodiments, the reacting performed at a pressure of from 5 bar to 100 bar.

In some embodiments, the method further includes activating the $CO_2$ hydrogenation catalyst by drying the $CO_2$ hydrogenation catalyst by heating to 400° C. to 600° C. under flowing nitrogen, and reducing the $CO_2$ hydrogenation catalyst by heating to 400° C. to 600° C. in the presence of a reducing gas mixture including hydrogen and substantially free of $CO_2$.

In some embodiments, the method includes an olefin having 2 to 4 carbon atoms selectivity of 15% to 45% based on a total number of moles of hydrocarbon mixture.

In some embodiments, the method has a $CO_2$ conversion of 20% to 40% based on a total number of moles of $CO_2$ introduced.

In some embodiments, the method has a hydrocarbon selectivity of 3% to 11% based on a total number of moles of $CO_2$ introduced.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
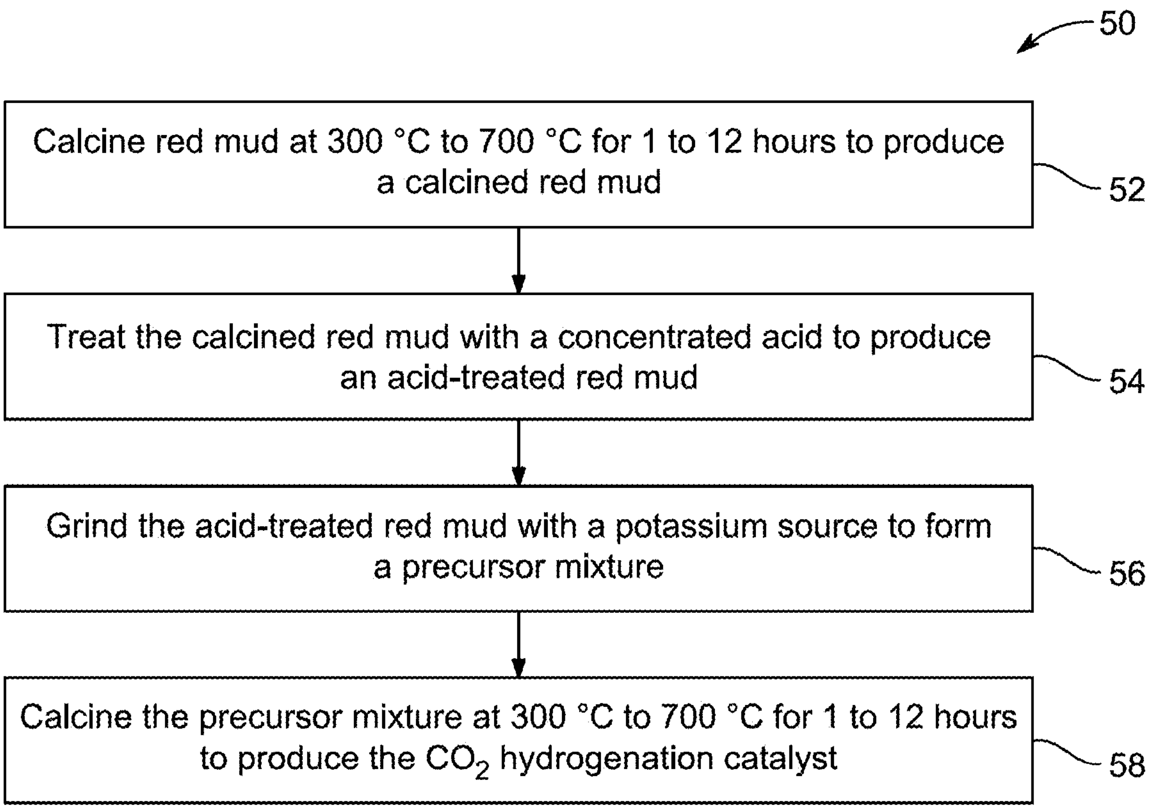
FIG. 1A is an exemplary flow chart of a method of forming a carbon dioxide ($CO_2$) hydrogenation catalyst, according to certain embodiments.
Figure 1B:
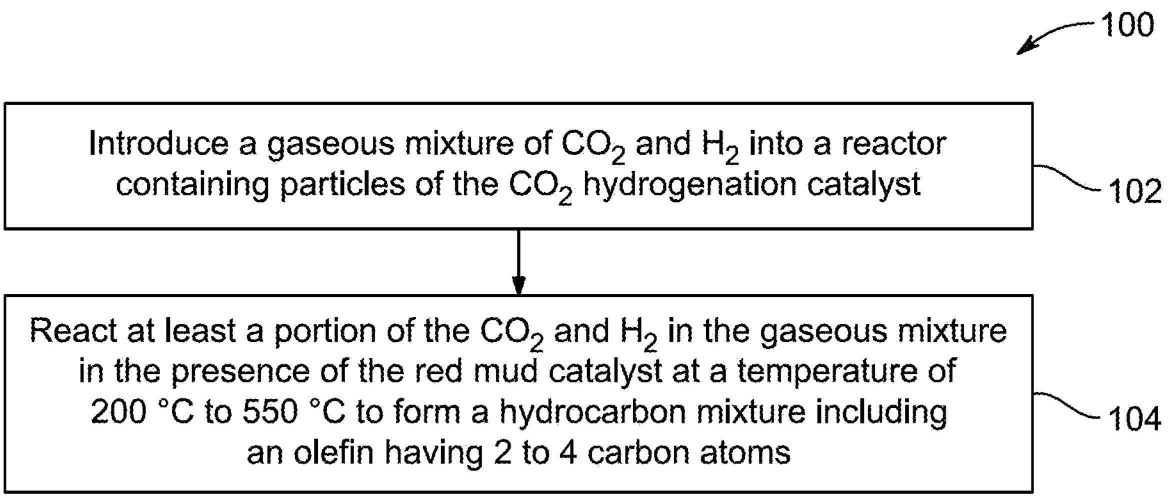
FIG. 1B is an exemplary flow chart of a method of hydrogenating $CO_2$, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Embodiments of the present disclosure will now be described more fully hereinafter with reference to the accompanying drawings, in which some, but not all embodiments of the disclosure are shown.

As used herein, the words "about," "approximately," or "substantially similar" may be used when describing magnitude and or position to indicate that the value and/or position described is within a reasonable expected range of values and/or positions. For example, a numeric value may have a value that is +/−0.1% of the stated value (or range of values), +/−1% of the slated value (or range of values), +/−2% of the stated value (or range of values), +/−5% of the slated value (or range of values), +/−10% of the staled value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

Hydrogen temperature-programmed reduction ($H_2$-TPR) is a technique used to study the reduction properties of catalysts or materials. Typically, the method involves exposing a sample to hydrogen gas while its temperature is gradually increased. The interaction between hydrogen and the material is monitored to identify the temperature at which the material is reduced (e.g., when metal oxides are converted into their metallic form). The data obtained can provide information related to the material's reducibility, the presence and identities of different metal species, and the catalyst's effectiveness in various reactions.

"Red mud" is a reddish-brown, highly alkaline byproduct generated during the extraction of alumina from bauxite ore using the Bayer process. It results from the chemical treatment of bauxite with sodium hydroxide (NaOH) under high temperature and pressure. Typically, red mud primarily consists of iron oxides (e.g., hematite), aluminum oxides, silica ($SiO_2$), other metal oxides (e.g., $TiO_2$, CaO), and alkali compounds (e.g., NaOH, $Na_2CO_3$).

"Sodalite" is a silicate mineral with the formula $Na_8(Al_6Si_6O_{24})Cl_2$. Sodalite has a structure that includes an aluminosilicate cage network with sodium cations and chloride anions located in interframework spaces such as void. The framework forms a zeolite-like cage structure.

"Muscovite" is a hydrated silicate mineral that includes aluminum and potassium. Typically, muscovite has a formula of $KAl_2(AlSi_3O_{10}(OH)_2)$. Muscovite is a phyllosilicate (sheet silicate) mineral and has a TOT-c structure. In which sheets containing a tetrahedral layer of silicon-oxygen tetrahedra and aluminum-oxygen tetrahedra, an octahedral layer of aluminum-oxygen octahedra, and a second tetrahedral layer are loosely bonded to each other by potassium cations.

As used herein, the term 'olefins,' also known as alkenes, are unsaturated hydrocarbons containing at least one carbon-carbon double bond in their molecular structure. The general formula for olefins is $C_nH_{2n}$, where 'n' is the number of carbon atoms. Due to their carbon-carbon double bond, olefins can undergo addition reactions, where atoms or groups of atoms are added to the carbon-carbon double bond and are therefore desirable and widely used feedstock chemicals across a wide variety of industries. Ethylene ($C_2H_4$) and propylene ($C_3H_6$) are common examples of olefins.

According to a first aspect, the present disclosure relates to a $CO_2$ hydrogenation catalyst. A $CO_2$ hydrogenation catalyst is a substance that facilitates the chemical reaction where carbon dioxide ($CO_2$) reacts with hydrogen ($H_2$) to produce value-added products, such as saturated hydrocarbons, alcohols, and/or olefins. These catalysts lower the activation energy of the reaction, making it more efficient and faster, typically under elevated temperatures and pressures. A primary goal of $CO_2$ hydrogenation is to convert $CO_2$, a greenhouse gas, into useful chemicals, contributing to energy production, alternative sources for feedstock chemicals, and carbon mitigation efforts.

In some embodiments, the $CO_2$ hydrogenation catalyst includes an alkali-metal enriched bauxite residue (red mud). In some embodiments, the $CO_2$ hydrogenation catalyst includes $CaCO_3$. In some embodiments, the $CO_2$ hydrogenation catalyst includes $Fe_2O_3$. In some embodiments, the $CO_2$ hydrogenation catalyst includes FeO(OH). In some embodiments, the $CO_2$ hydrogenation catalyst includes $Al(OH)_3$. In some embodiments, the $CO_2$ hydrogenation catalyst includes sodalite. In some embodiments, the $CO_2$ hydrogenation catalyst includes muscovite. In some embodiments, the $CO_2$ hydrogenation catalyst includes $Na_5Al_2CSi_3O_{15}$. In some embodiments, the $CO_2$ hydrogenation catalyst includes $CaCO_3$, $Fe_2O_3$, FeO(OH), $Al(OH)_3$, sodalite, muscovite, and $Na_5Al_2CSi_3O_{15}$.

In general, the $Fe_2O_3$may be any suitable phase of $Fe_2O_3$. Examples oof phases of $Fe_2O_3$ include, but are not limited to $\alpha$-$Fe_2O_3$, $\beta$-$Fe_2O_3$, $\gamma$-$Fe_2O_3$, and $\varepsilon$-$Fe_2O_3$. In some embodiments, the $Fe_2O_3$ is $\alpha$-$Fe_2O_3$.

In some embodiments, the $CO_2$ hydrogenation catalyst includes 1 to 10 wt % potassium based on the total weight of $CO_2$ hydrogenation catalyst. For example, the $CO_2$ hydrogenation catalyst can include 1.0 wt %, 1.25 wt %, 1.5 wt %, 1.75 wt %, 2.0 wt %, 2.25 wt %, 2.5 wt %, 2.75 wt %, 3.0 wt %, 3.25 wt %, 3.5 wt %, 3.75 wt %, 4.0 wt %, 4.25 wt %, 4.5 wt %, 4.75 wt %, 5.0 wt %, 5.25 wt %, 5.5 wt %, 5.75 wt %, 6.0 wt %, 6.25 wt %, 6.5 wt %, 6.75 wt %, 7.0 wt %, 7.25 wt %, 7.5 wt %, 7.75 wt %, 8.0 wt %, 8.25 wt %, 8.5 wt %, 8.75 wt %, 9.0 wt %, 9.25 wt %, 9.5 wt %, 9.75 wt %, or 10 wt % potassium. In general, the amount of potassium can be measured by any suitable method or technique known to one of ordinary skill in the art. In some embodiments, the amount of potassium is measured by inductively coupled plasma optical emission spectroscopy (ICP-OES). The inclusion of potassium in this amount may be advantageous for enhancing catalytic properties. Such enhancement may involve improving $CO_2$ adsorption, increasing reactivity, increasing stability, improving olefin selectivity, and/or increasing the $CO_2$ conversion.

In some embodiments, the $CO_2$ hydrogenation catalyst further includes alumina. In general, the alumina may be present in any suitable form or phase. Examples of forms or phases of alumina include, but are not limited to $\alpha$-alumina, $\gamma$-alumina, $\eta$-alumina, and $\delta$-alumina.

In some embodiments, the $CO_2$ hydrogenation catalyst further comprises $TiO_2$. In general, the $TiO_2$ may exist in various phases, including anatase, rutile, and brookite. In some embodiments, the $TiO_2$ is present in the rutile phase.

In some embodiments, the $CO_2$ hydrogenation catalyst further includes alumina and $TiO_2$.

In some embodiments, the $CO_2$ hydrogenation catalyst may further include other metal oxide(s) such as NiO, CuO, $Cu_2O$, $CeO_2$, and $ZrO_2$.

In some embodiments, the $CO_2$ hydrogenation catalyst is in the form of particles. In general, the particles can be any shape known to one of ordinary skill in the art. Examples of suitable shapes the particles may take include spheres, spheroids, lentoids, ovoids, solid polyhedra such as tetrahedra, cubes, octahedra, icosahedra, dodecahedra, hollow polyhedra (also known as nanocages), stellated polyhedra (both regular and irregular, also known as nanostars), triangular prisms (also known as nanotriangles), hollow spherical shells (also known as nanoshells), tubes (also known as nanotubes), nanosheets, nanoplatelets, nanodisks, rods (also known as nanorods), belts (also known as nanobelts), ribbons (also known as nanoribbons), and mixtures thereof. In the case of nanorods, the rod shape may be defined by a ratio of a rod length to a rod width, the ratio being known as the aspect ratio. For particles of the current invention, nanorods should have an aspect ratio less than 1000, preferably less than 750, preferably less than 500, preferably less than 250, preferably less than 100, preferably less than 75, preferably less than 50, preferably less than 25.

In some embodiments, the particles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of particles having a different shape. As used herein, the term "non-uniform shape" refers to an average consistent shape that differs by more than 10% of the distribution of particles having a different shape. In one embodiment, the shape is uniform and at least 90% of the particles are spherical or substantially circular, and less than 10% are polygonal. In another embodiment, the shape is non-uniform and less than 90% of the particles are spherical or substantially circular, and greater than 10% are polygonal.

In some embodiments, the particles have a mean particle size of 0.1 to 10 μm. For example, the particles may have a mean particle size of 0.1 μm, 0.25 μm, 0.5 μm, 0.75 μm, 1.0 μm, 1.25 μm, 1.5 μm, 1.75 μm, 2.0 μm, 2.25 μm, 2.5 μm, 2.75 μm, 3.0 μm, 3.25 μm, 3.5 μm, 3.75 μm, 4.0 μm, 4.25 μm, 4.5 μm, 4.75 μm, 5.0 μm, 5.25 μm, 5.5 μm, 5.75 μm, 6.0 μm, 6.25 μm, 6.5 μm, 6.75 μm, 7.0 μm, 7.25 μm, 7.5 μm, 7.75 μm, 8.0 μm, 8.25 μm, 8.5 μm, 8.75 μm, 9.0 μm, 9.25 μm, 9.5 μm, 9.75 μm, or 10.0 μm. In embodiments where the particles are spherical, the particle size may refer to a particle diameter. In embodiments where the particles are polyhedral or some other non-spherical shape, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the particles have an anisotropic shape such as nanorods, the particle size may refer to a length of the nanorod, a width of the nanorod, or an average of the length and width of the nanorod. In some embodiments in which the particles have non-spherical shapes, the particle size refers to the diameter of a sphere having an equivalent volume as the particle. In some embodiments in which the particles have non-spherical shapes, the particle size refers to the diameter of a sphere having an equivalent diffusion coefficient as the particle.

In some embodiments, the particles of the present disclosure are monodisperse, having a coefficient of variation or relative standard deviation, expressed as a percentage and defined as the ratio of the particle size standard deviation (a) to the particle size mean (p) multiplied by 100 of less than 25%, preferably less than 10%, preferably less than 8%, preferably less than 6%, preferably less than 5%, preferably less than 4%, preferably less than 3%, preferably less than 2%. In some embodiments, the particles of the present disclosure are monodisperse having a particle size distribution ranging from 80% of the average particle size to 120% of the average particle size, preferably 90-110%, preferably 95-105% of the average particle size. In some embodiments, the particles are not monodisperse.

In general, the particle size may be determined by any suitable method known to one of ordinary skill in the art. In some embodiments, the particle size is determined by powder X-ray diffraction (PXRD). Using PXRD, the particle size may be determined using the Scherrer equation, which relates the full-width at half-maximum (FWHM) of diffraction peaks to the size of regions comprised of a single crystalline domain (known as crystallites) in the sample. In some embodiments, the crystallite size is the same as the particle size. For accurate particle size measurement by PXRD, the particles should be crystalline, comprise only a single crystal, and lack non-crystalline portions. Typically, the crystallite size underestimates particle size compared to other measures due to factors such as amorphous regions of particles, the inclusion of non-crystalline material on the surface of particles such as bulky surface ligands, and particles which may be composed of multiple crystalline domains. In some embodiments, the particle size is determined by dynamic light scattering (DLS). DLS is a technique which uses the time-dependent fluctuations in light scattered by particles in suspension or solution in a solvent, typically water to measure a size distribution of the particles. Due to the details of the DLS setup, the technique measures a hydrodynamic diameter of the particles, which is the diameter of a sphere with an equivalent diffusion coefficient as the particles. The hydrodynamic diameter may include factors not accounted for by other methods such as non-crystalline material on the surface of particles such as bulky surface ligands, amorphous regions of particles, and surface ligand-solvent interactions. Further, the hydrodynamic diameter may not accurately account for non-spherical particle shapes. DLS does have an advantage of being able to account for or more accurately model solution or suspension behavior of the particles compared to other techniques. In some embodiments, the particle size is determined by electron microscopy techniques such as scanning electron microscopy (SEM) or transmission electron microscopy (TEM).

In some embodiments, the $CO_2$ hydrogenation catalyst has a surface area of 10 to 20 $m^2/g$. For example, the $CO_2$ hydrogenation catalyst may have a surface area of 10.1 $m^2/g$, 10.2 $m^2/g$, 10.3 $m^2/g$, 10.4 $m^2/g$, 10.5 $m^2/g$, 10.6 $m^2/g$, 10.7 $m^2/g$, 10.8 $m^2/g$, 10.9 $m^2/g$, 11.0 $m^2/g$, 11.1 $m^2/g$, 11.2 $m^2/g$, 11.3 $m^2/g$, 11.4 $m^2/g$, 11.5 $m^2/g$, 11.6 $m^2/g$, 11.7 $m^2/g$, 11.8 $m^2/g$, 11.9 $m^2/g$, 12.0 $m^2/g$, 12.1 $m^2/g$, 12.2 $m^2/g$, 12.3 $m^2/g$, 12.4 $m^2/g$, 12.5 $m^2/g$, 12.6 $m^2/g$, 12.7 $m^2/g$, 12.8 $m^2/g$, 12.9 $m^2/g$, 13.0 $m^2/g$, 13.1 $m^2/g$, 13.2 $m^2/g$, 13.3 $m^2/g$, 13.4 $m^2/g$, 13.5 $m^2/g$, 13.6 $m^2/g$, 13.7 $m^2/g$, 13.8 $m^2/g$, 13.9 $m^2/g$, 14.0 $m^2/g$, 14.1 $m^2/g$, 14.2 $m^2/g$, 14.3 $m^2/g$, 14.4 $m^2/g$, 14.5 $m^2/g$, 14.6 $m^2/g$, 14.7 $m^2/g$, 14.8 $m^2/g$, 14.9 $m^2/g$, 15.0 $m^2/g$, 15.1 $m^2/g$, 15.2 $m^2/g$, 15.3 $m^2/g$, 15.4 $m^2/g$, 15.5 $m^2/g$, 15.6 $m^2/g$, 15.7 $m^2/g$, 15.8 $m^2/g$, 15.9 $m^2/g$, 16.0 $m^2/g$, 16.1 $m^2/g$, 16.2 $m^2/g$, 16.3 $m^2/g$, 16.4 $m^2/g$, 16.5 $m^2/g$, 16.6 $m^2/g$, 16.7 $m^2/g$, 16.8 $m^2/g$, 16.9 $m^2/g$, 17.0 $m^2/g$, 17.1 $m^2/g$, 17.2 $m^2/g$, 17.3 $m^2/g$, 17.4 $m^2/g$, 17.5 $m^2/g$, 17.6 $m^2/g$, 17.7 $m^2/g$, 17.8 $m^2/g$, 17.9 $m^2/g$, 18.0 $m^2/g$, 18.1 $m^2/g$, 18.2 $m^2/g$, 18.3 $m^2/g$, 18.4 $m^2/g$, 18.5 $m^2/g$, 18.6 $m^2/g$, 18.7 $m^2/g$, 18.8 $m^2/g$, 18.9 $m^2/g$, 19.0 $m^2/g$, 19.1 $m^2/g$, 19.2 $m^2/g$, 19.3 $m^2/g$, 19.4 $m^2/g$, 19.5 $m^2/g$, 19.6 $m^2/g$, 19.7 $m^2/g$, 19.8 $m^2/g$, 19.9 $m^2/g$, or 20.0 $m^2/g$. In some embodiments, the surface area may depend on or be associated with the potassium content of the $CO_2$ hydrogenation catalyst. In some embodiments, the $CO_2$ hydrogenation catalyst includes 1% K and has a surface area of 14.19 $m^2/g$. In some embodiments, the $CO_2$ hydrogenation catalyst includes 3% K and has a surface area of 15.26 $m^2/g$. In some embodiments, the $CO_2$ hydrogenation catalyst includes 5% K and has a surface area of 11.2 $m^2/g$.

In some embodiments, the $CO_2$ hydrogenation catalyst has a pore volume of 0.015 to 0.030 $cm^3/g$. For example, the $CO_2$ hydrogenation catalyst may have a pore volume of 0.015 $cm^3/g$, 0.016 $cm^3/g$, 0.017 $cm^3/g$, 0.018 $cm^3/g$, 0.019 $cm^3/g$, 0.020 $cm^3/g$, 0.021 $cm^3/g$, 0.022 $cm^3/g$, 0.023 $cm^3/g$, 0.024 $cm^3/g$, 0.025 $cm^3/g$, 0.026 $cm^3/g$, 0.027 $cm^3/g$, 0.028 $cm^3/g$, 0.029 $cm^3/g$, or 0.030 $cm^3/g$. In some embodiments, the pore volume may depend on or be associated with the potassium content of the $CO_2$ hydrogenation catalyst. In some embodiments, the $CO_2$ hydrogenation catalyst includes 1% K has a pore volume of 0.026 $cm^3/g$. In some embodiments, the $CO_2$ hydrogenation catalyst includes 3% K has a pore volume 0.023 $cm^3/g$. In some embodiments, the $CO_2$ hydrogenation catalyst includes 5% K has a pore volume 0.019 $cm^3/g$.

The present disclosure also relates to a method of forming the $CO_2$ hydrogenation catalyst. FIG. 1A illustrates a flow chart of a method 50 of forming the $CO_2$ hydrogenation catalyst. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes calcining red mud to produce a calcined red mud. In some embodiments, the calcining is performed at 300 to 700° C., preferably 325 to 675° C., preferably 350 to 650° C., preferably 375 to 625° C., preferably 400 to 600° C., preferably 425 to 575° C., preferably 450 to 550° C., preferably 475 to 525° C., preferably 500° C. In some embodiments, the calcining is performed for 1 to 12 hours, preferably 2 to 8 hours, preferably 3 to 7 hours, preferably 4 to 6 hours, preferably 5 hours. Generally, calcination is carried out by heating it to a high temperature under a restricted supply of ambient oxygen. Typically, the calcination is carried out in a furnace, preferably equipped with a temperature control system, which may provide a heating rate of up to 50° C./min, preferably up to 40° C./min, preferably up to 30° C./min, preferably up to 20° C./min, preferably up to 10° C./min, preferably up to 5° C./min, preferably up to 3° C./min.

At step 54 the method 50 includes treating the calcined red mud with a concentrated acid to produce an acid-treated red mud. In some embodiments, concentrated acid may include, but is not limited to, sulfuric acid, nitric acid, phosphoric acid, hydrochloric acid, hydrofluoric acid, perchloric acid, acetic acid, formic acid, tartaric acid, citric acid, lactic acid, oxalic acid, malic acid, trifluoroacetic acid, benzoic acid, sulfurous acid, peracetic acid, stearic acid, glutaric acid, and butyric acid. In some embodiments, the concentrated acid is HCl, having a concentration of 30% to 38%, preferably 32 to 37.5%, preferably 37% by weight in water.

At step 56, the method 50 includes grinding the acid-treated red mud with a potassium source to form a precursor mixture. In general, the grinding may be carried out using any suitable means. Examples of suitable such means include, but are not limited to ball milling, blending, etc., using manual method (e.g., mortar) or machine-assisted methods such as using a mechanical blender, or any other apparatus known to those of ordinary skill in the art. In some embodiments, the acid-treated red mud is ground with the potassium source using mortar-pestle.

In some embodiments, the sources of potassium may include, but is not limited to, potassium nitrate, potassium carbonate, potassium chloride, potassium sulfate, potassium acetate, and potassium phosphate. In some embodiments, the potassium source includes potassium nitrate. In some embodiments, the potassium source is substantially free of potassium hydroxide.

Using a potassium source free of potassium hydroxide may be advantageous for increasing the catalyst's chemical integrity by preventing excessive alkalinity.

At step 58, the method 50 includes calcining the precursor mixture to produce the $CO_2$ hydrogenation catalyst. In some embodiments, the calcining is performed at 300 to 700° C., preferably 325 to 675° C., preferably 350 to 650° C., preferably 375 to 625° C., preferably 400 to 600° C., preferably 425 to 575° C., preferably 450 to 550° C., preferably 475 to 525° C., preferably 500° C. In some embodiments, the calcining is performed for 1 to 12 hours, preferably 2 to 8 hours, preferably 3 to 7 hours, preferably 4 to 6 hours, preferably 5 hours.

The present disclosure also relates to a method of hydrogenating carbon dioxide. FIG. B illustrates a flow chart of a method 70 of hydrogenating carbon dioxide. The order in which the method 70 is described is not intended to be construed as a limitation, and any number of the described method steps can be combined in any order to implement the method 70. Additionally, individual steps may be removed or skipped from the method 70 without departing from the spirit and scope of the present disclosure.

In some embodiments, at step 72, the method 70 includes activating the $CO_2$ hydrogenation catalyst. In some embodiments, the $CO_2$ hydrogenation catalyst is activated by a process including drying the $CO_2$ hydrogenation catalyst by heating it to 400 to 600° C., preferably 425 to 575° C., preferably 450 to 550° C., preferably 475 to 525° C., preferably 500° C. under flowing nitrogen and reducing the $CO_2$ hydrogenation catalyst by heating to 400 to 600° C., preferably 425 to 575° C., preferably 450 to 550° C., preferably 475 to 525° C., preferably 500° C. in the presence of a reducing gas mixture including hydrogen and substantially free of $CO_2$.

At step 74, the method 70 includes introducing a gaseous mixture of $CO_2$ and $H_2$ into a reactor containing particles of the $CO_2$ hydrogenation catalyst. In some embodiments, the gaseous mixture may also include other gases, such as CO, $N_2$, argon, and the like in addition to $CO_2$ and $H_2$. In some embodiments, the gaseous mixture, including $CO_2$ and $H_2$, is introduced into the reactor having a volumetric ratio of $CO_2$:$H_2$ of 1:10 to 10:1, preferably in a range of 1:1 to 1:6, preferably 1:5, preferably 1:4, preferably 1:3.

In general, the reactor may be any suitable type of reactor. Examples of suitable reactors include, but are not limited to a fixed-bed reactor, a trickle-bed reactor, a moving bed reactor, a rotating bed reactor, a fluidized bed reactor, a tumbler reactor, and a slurry reactor. In some embodiments, the reactor may be a fixed-bed reactor in the form of a vertical cylindrical reactor which includes a top portion, a vertically oriented cylindrical body portion, a bottom portion, a housing. In some embodiments, the housing has an open top, and open bottom supportably maintained with the vertically oriented cylindrical body portion. In some embodiments, the $CO_2$ hydrogenation catalyst is supportably retained within the housing, permitting fluid flow therethrough. In some embodiments, the vertical cylindrical reactor further includes at least one propeller agitator disposed in the bottom portion of the reactor. The propeller agitator may be useful for homogenization, dispersion, and suspension of the $CO_2$ hydrogenation particles. In some embodiments, bottom portion is cone-shaped or pyramidal. In some embodiments, the bottom portion may have a cylindrical, cubical, cuboidal, or rhombic shape. In some embodiments, a plurality of recirculation tubes fluidly connects the bottom portion of the vertical cylindrical reactor with the vertically oriented cylindrical body portion of the vertical cylindrical reactor. In some embodiments, the fixed-bed reactor may be made up of a material such as stainless-steel, iron, aluminum, copper, lead, iron, zirconium, or another alloy.

At step 76, the method 70 includes reacting at least a portion of the $CO_2$ and $H_2$ in the gaseous mixture in the presence of the $CO_2$ hydrogenation catalyst at a temperature of 200 to 550° C. to form a hydrocarbon mixture including an olefin having 2 to 4 carbon atoms. For example, the reacting may be performed at 200° C., 225° C., 250° C., 275° C., 300° C., 325° C., 350° C., 375° C., 400° C., 425° C., 450° C., 475° C., 500° C., 525° C., or 550° C. In some embodiments, the reacting is performed at a pressure of 5 to 100 bar. For example, the reacting may be performed at 5 bar, 7.5 bar, 10 bar, 12.5 bar, 15 bar, 17.5 bar, 20 bar, 22.5 bar, 25 bar, 27.5 bar, 30 bar, 32.5 bar, 35 bar, 37.5 bar, 40 bar, 42.5 bar, 45 bar, 47.5 bar, 50 bar, 52.5 bar, 55 bar, 57.5 bar, 60 bar, 62.5 bar, 65 bar, 67.5 bar, 70 bar, 72.5 bar, 75 bar, 77.5 bar, 80 bar, 82.5 bar, 85 bar, 87.5 bar, 90 bar, 92.5 bar, 95 bar, 97.5 bar, or 100 bar.

In some embodiments, the hydrocarbon mixture includes an olefin having 2 to 4 carbon atoms. Examples of olefins having 2 to 4 carbon atoms include, but are not limited to ethylene (ethene), propylene (propene), 1-butene, 2-butene, and butadiene. In some embodiments, the hydrocarbon mixture may further include a saturated hydrocarbon such as methane, ethane, propane, butane, and pentane; an aromatic hydrocarbon such as benzene, naphthalene, anthracene; an alcohol such as methanol and ethanol; and/or combinations thereof. In some embodiments, the method has a selectivity for the olefin having 2 to 4 carbon atoms of 15 to 45% based on the total number of moles of the hydrocarbon mixture. For example, the selectivity can be 15%, 17.5%, 20%, 22.5%, 25%, 27.5%, 30%, 32.5%, 35%, 37.5%, 40%, 42.5%, or 45%.

In some embodiments, the method 70 has a $CO_2$ conversion of 20 to 40% based on a total number of moles of $CO_2$ introduced. For example, the method may have a $CO_2$ conversion of 20%, 22.5%, 25%, 27.5%, 30%, 32.5%, 35%, 37.5%, or 40%. In some embodiments, the method 70 has a hydrocarbon selectivity of 3 to 11%, based on a total number of moles of $CO_2$ converted by the method. For example, the method may have a hydrocarbon selectivity of 3%, 4%, 5%, 6%, 7%, 8%, 9%, 10%, or 11%.

In some embodiments, the $CO_2$ hydrogenation catalyst has a hydrogen temperature-programmed reduction ($H_2$-TPR) of 400 to 600 μmoles per gram (μmol/g) at a temperature of 200 to 850° C. For example, the $H_2$-TPR can be 400 μmol/g, 410 μmol/g, 420 μmol/g, 430 μmol/g, 440 μmol/g, 450 μmol/g, 460 μmol/g, 470 μmol/g, 480 μmol/g, 490 μmol/g, 500 μmol/g, 510 μmol/g, 520 μmol/g, 530 μmol/g, 540 μmol/g, 550 μmol/g, 560 μmol/g, 570 μmol/g, 580 μmol/g, 590 μmol/g, or 600 μmol/g. In some embodiments, the $H_2$-TPR may depend on or be associated with the potassium content of the $CO_2$ hydrogenation catalyst. In some embodiments, the $CO_2$ hydrogenation catalyst includes 1% K and has a $H_2$-TPR of 497 μmol/g. In some embodiments, the $CO_2$ hydrogenation catalyst includes 2% K and has a $H_2$-TPR of 488 μmol/g. In some embodiments, the $CO_2$ hydrogenation catalyst includes 3% K and has a $H_2$-TPR of 423 to 439 μmol/g.

EXAMPLES

The following examples demonstrate a carbon dioxide ($CO_2$) hydrogenation catalyst, a method of production thereof, and a method of $CO_2$ hydrogenation using the synthesized catalyst. The examples are provided solely for illustration and are not to be construed as limitations of the present disclosure, as many variations are possible without departing from the spirit and scope of the present disclosure.

Example 1: Reagents and Chemicals

The materials and chemicals were used without further purification. The chemicals included raw red mud (RM) from Ma'aden bauxite and alumina company (MBAC) of Saudi Arabia, deionized water (DI-$H_2O$), and different metal salts including sodium chloride (NaCl, Sigma Aldrich), potassium nitrate ($KNO_3$), cesium hydroxide (CsOH), magnesium oxide (MgO), barium oxide (BaO), and strontium chloride ($SrCl_2$), potassium hydroxide (KOH), hydrochloric acid (HCl).

Example 2: Catalyst Preparation

The raw RM was dried in an oven at 80° C., ground, and sieved to a size of less than (<) 200 micrometer (μm). In addition, the RM catalysts was prepared using a uniform catalyst fabrication process. In particular, 10 millilitres (mL) of concentrated HCl was added to a well-dispersed suspension of 3 grams (g) of calcined RM in 50 mL of DI-$H_2O$, followed by stirring at 250 revolutions per minute (rpm) overnight. The neutralized RM was then filtered, washed with DI-$H_2O$, and dried in the oven at 80° C., overnight. RM was grounded and obtained as 1.6 gm of HCl-treated RM.

Example 3: Preparation of K-Promoted Red Mud (K@RM) Catalysts

A series of alkali metal promoters, including sodium (N a), potassium (K), magnesium (Mg), barium (Ba), cesium (Cs), and strontium (Sr), each at 3 weight percent (wt %), were ground using a mortar and pestle with calcined red mud (RM) for 30 minutes. The resulting solid mixtures were calcined at 500° C. with a heating rate of 3° C./min and a holding time of 5 hours. The catalysts were designated as 3 wt % M@RM (where M represents N a, K, Mg, Ba, Cs, or Sr). For potassium, 3 wt % K was added from two different sources including potassium nitrate ($KNO_3$) and potassium hydroxide (KOH). Further, potassium-promoted catalysts with varying weight percentages of 1 wt %, 2 wt %, 3 wt %, and 5 wt %, were prepared using $KNO_3$ following the same procedure as described above. The obtained catalysts were denoted as 1 wt % K@RM, 2 wt % K@RM, 3 wt % K@RM, and 5 wt % K@RM.

Example 4: Catalytic Physiochemical Properties

A plurality of analytical techniques were employed to characterize various properties of the obtained samples. X-ray diffraction (XRD) of red mud (RM) and metal-promoted RM catalysts were obtained using Cu—$K_\alpha$ radiation with a Rigaku Ultima-IV diffractometer operating at 40 kV and 25 mA. The XRD scan covered a range from 5° to 70° (2θ) with a step size of 0.02° at a scanning speed of 2° per minute. Further, Fourier transform infrared spectroscopy (FTIR) was utilized, which is a fingerprint technique used to identify the surface functional groups of catalysts. The interaction of materials with infrared irradiation induces stretching and vibrations in specific chemical bonds, which are analyzed using FTIR. Further, FTIR analysis was performed using potassium bromide (KBr) as the IR-transparent window material for sample preparation. The IR transmission spectra was recorded across a wavenumber range of 500 $cm^{-1}$ to 4000 $cm^{-1}$. Furthermore, nitrogen ($N_2$) adsorption-desorption isotherm was used to calculate the Brunauer-Emmett-Teller (BET) surface area and evaluate the catalytic surface area, pore volume, micropore volume, and mesopore volume using ASA P2020 (Micromeritics, USA). Inductively coupled plasma optical emission spectrometry (ICP-OES) was performed using the PlasmaQuant PO 9000 system (Analytik Jena) to quantify the specific elemental composition of red mud (RM). Samples were digested in a dilute solution of nitric acid ($HNO_3$) and HCl prior to analysis. Calibration curves for silicon (Si), aluminum (Al), iron (Fe), and titanium (Ti) were prepared using ICP element standard solutions (Merck). Moreover, Raman spectroscopy was utilized to analyze and evaluate the catalyst surface before the reaction, and Raman spectra were recorded using a 455 nanometers (nm) DX R laser with a thermo scientific DX R Raman spectroscope. In addition, hydrogen temperature-programmed-reduction ($H_2$-TPR), using the BELCAT II from MacrotracBEL, was used to observe the reduction capability of catalysts by $H_2$. $H_2$-TPR was performed by placing 50 mg of catalyst in a reactor tube. The sample was preheated at 500° C. for 30 minutes under an argon flow of 50 milliliters per minute (mL/min). After cooling the reactor to 50° C., a gas mixture of hydrogen ($H_2O$) and argon (Ar) was introduced into the reactor tube. The mixture included 10% of $H_2$ at a flow rate of 5 mL/min, and 90% argon at a flow rate of 50 mL/min. Further, the sample was heated to 900° C. at a rate of 10° C./min while the TCD signal was captured concurrently.

Example 5: Catalyst Structure and Morphology

Further analyses were conducted using a field emission scanning electron microscope (FESEM) (Lyra3, Tescan, Czech Republic) with an operating voltage of 20 kV for visual observation of the particle size and surface morphology of the catalysts. The SEM samples were prepared by pipetting the ethanolic sample onto alumina stubs and further the stubs were Au-coated using an automated Au-coater (Quorum, Q150T E). Energy dispersive spectroscopy (EDS)

spectra, elemental analysis, and mapping were carried out using an SEM Lyra 3 accessories. High-resolution transmission electron microscopy (HR-TEM) (JEM 2100F, JEOL), operating at 200 kV acceleration voltage, was used to identify the size and shape of each element present in the catalysts, as well as the structural characterizations such as crystallinity, and planner orientations of different metals. The ethanolic suspension containing the catalyst was poured onto the copper grid that was placed at room temperature.

Example 6: Catalytic Activity Evaluation Method

The RM catalysts with different promoters were evaluated for $CO_2$ hydrogenation inside a fixed bed reactor (PID Microactivity-Effireactor). For each experiment, 0.20 g of the catalyst was placed inside a stainless steel 316 (SS316) tube with an inner diameter of 9.11 mm, at a specific location within the 300 mm long tube. The catalyst sample was heated at 500° C. for 50 minutes with 20 mL/min $N_2$ gas to eliminate moisture as moisture increases the reaction barrier for $CO_2$. The catalysts were reduced in the presence of $H_2$ gas at a flow rate of 3 mL/min for 30 minutes. The sample was cooled to 150° C. Further, the reactor tube was pressurized to 30 bar with a $CO_2/H_2$ molar ratio of 1:3 and heated to a reaction temperature of about 375° C. The catalytic evaluation was investigated at gas hourly space velocity (GHSV) of 4500 milliliters per gram per hour ($mL\cdot g^{-1}\cdot h^{-1}$). The evaluation of catalysts was conducted using an online gas chromatography (GC) system (Shimadzu, GC-2014) equipped with two flammable ionization detectors (FIDs) and a thermal conductivity detector (TCD). The first FID tracked anticipated hydrocarbons, and aromatics, while the second FID monitored oxygenates and acidic products. The TCD detector monitored permanent gases and catalytic conversions. Equation 1, equation 2, and equation 3 were used to determine $CO_2$ conversion and hydrocarbon selectivity on a carbon atom basis:

$$\text{Conv. of } CO_2 = \frac{CO_{2\,inlet} - CO_{2\,outlet}}{CO_{2\,inlet}} \times 100\% \quad (1)$$

$$\text{Sel. of } CO = \frac{CO_{outlet}}{CO_{2\,inlet} - CO_{2\,outlet}} \times 100\% \quad (2)$$

$$\text{Sel. of } C_nH_m = \frac{n\ C_nH_m}{CO_{2\,inlet} - CO_{2\,outlet} - CO_{inlet}} \times 100\% \quad (3)$$

where '$C_nH_m$' indicates moles of hydrocarbon created by outlet reaction with n carbons. '$CO_{2inlet}$' and '$CO_{2outlet}$' indicate moles of $CO_2$, and '$CO_{outlet}$' displays moles of CO.

Example 7: Physical and Chemical Characterization

The RM was treated with hydrochloric acid (HCl), followed by calcination to enhance physicochemical properties of the RM, which may influence the catalytic activity of the RM. The major component of RM includes Si, Fe, Al, Na, Ti, and Ca. The corresponding elemental quantifications were measured using ICP-OES. The analysis revealed that the Ca and Na contents decreased significantly in the acid-treated samples, which resulted in the formation of a modified RM structure. The observation was corroborated by the BET surface area data. The reduction in certain elements may be attributed to the higher dissolution of alkali metal ions in the acidic solution during the treatment process.

Figure 2A:
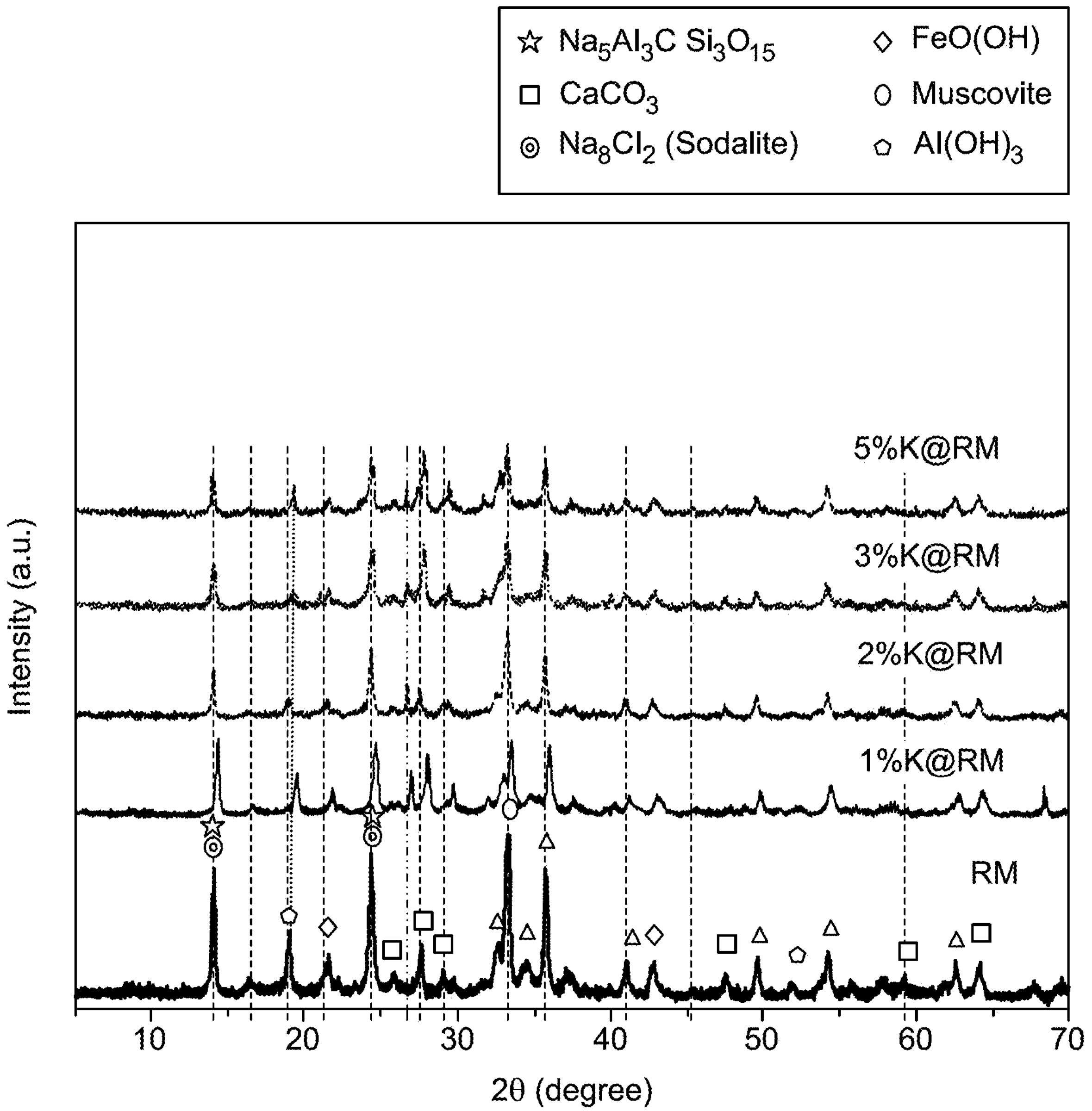
FIG. 2A shows X-ray diffraction (XRD) peaks for pure RM, 1 wt. % potassium (K) promoted RM (1% K@RM), 2% K@RM, 3% K@RM, and 5% K@RM, according to certain embodiments.
Figure 2B:
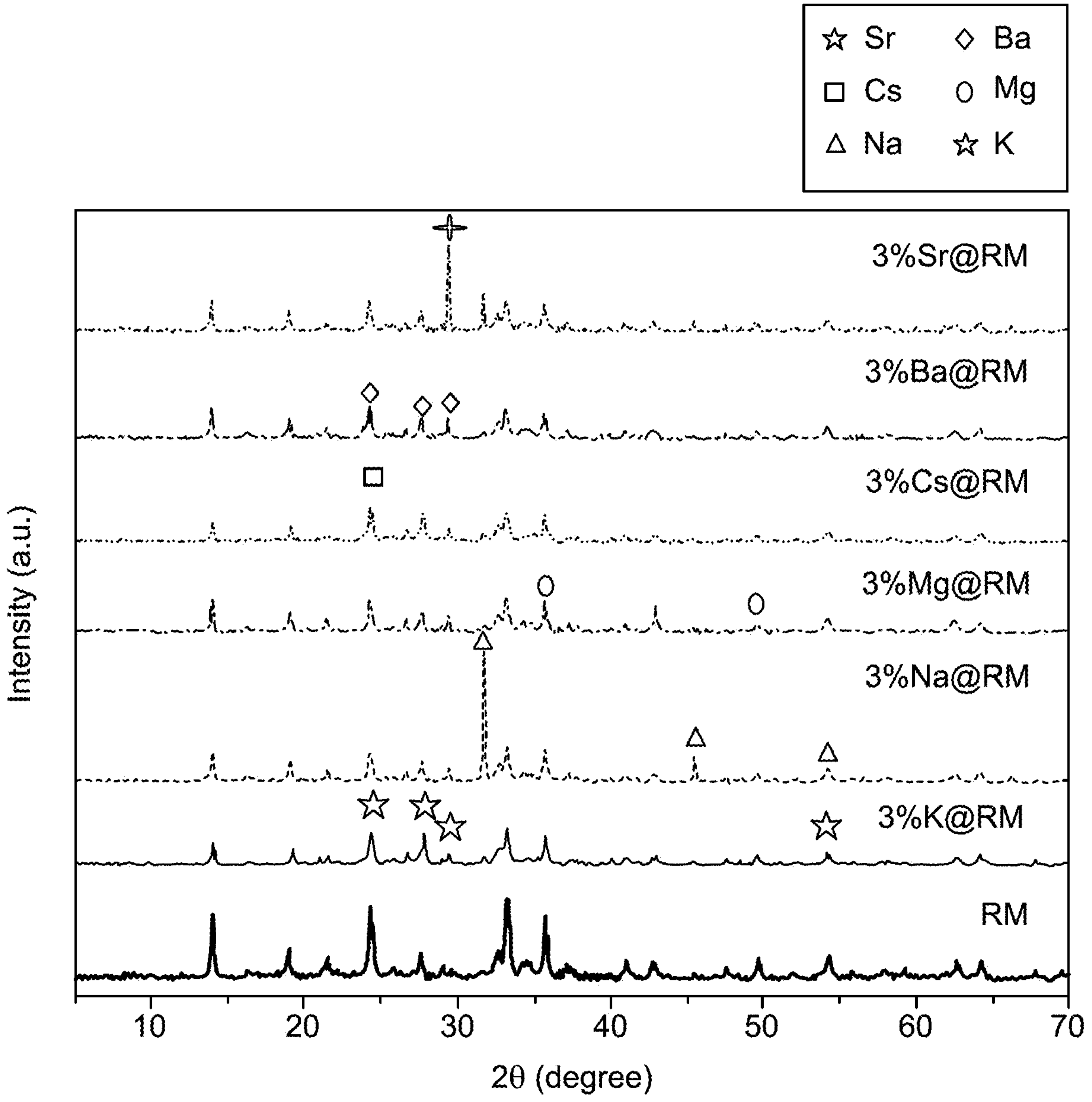
FIG. 2B shows XRD peaks for pure RM, and different metal promoted RM catalyst at 3 percent by weight of the metal, according to certain embodiments.

The crystallinity and composition of pure RM and metal-promoted RM were examined using XRD technique, as shown FIGS. 2A-2B. The XRD pattern for RM showed the existence of the primary mineral phases in the RM as $Fe_2O_3$, $Al_2O_3$, and $TiO_2$ [Li, X., et. al, Minerals, 13, 737, 2023; Mymrin, V., et. al., Green Chem., 5, 357-360, 2003; and Qi, Y., J Phys Conf Ser, 1759, 012004, 2021, each of which is incorporated herein by reference in its entirety]. The principal crystalline phases of $\alpha$-$Fe_2O_3$, AlO(OH), $A(OH)_3$, $CaCO_3$, $NasCl_2$ and $TiO_2$ were detected in XRD, as shown in FIG. 2A. In an example, calcium carbonate in the form of calcite ($CaCO_3$) was identified by diffraction peaks at $2\theta$ of about 26°, 27°, 28°, 48°, and 59°, and $Fe_2O_3$ peaks of about 34°, 36°, 42°, 49.5°, 54°, and 63°. The effect of K loading on the XRD pattern was evaluated, as the K content increased from 1% to 5%, a reduction in the intensity of reflection peaks associated with all metal planes was observed, as depicted in FIG. 2A.

Figure 3A:
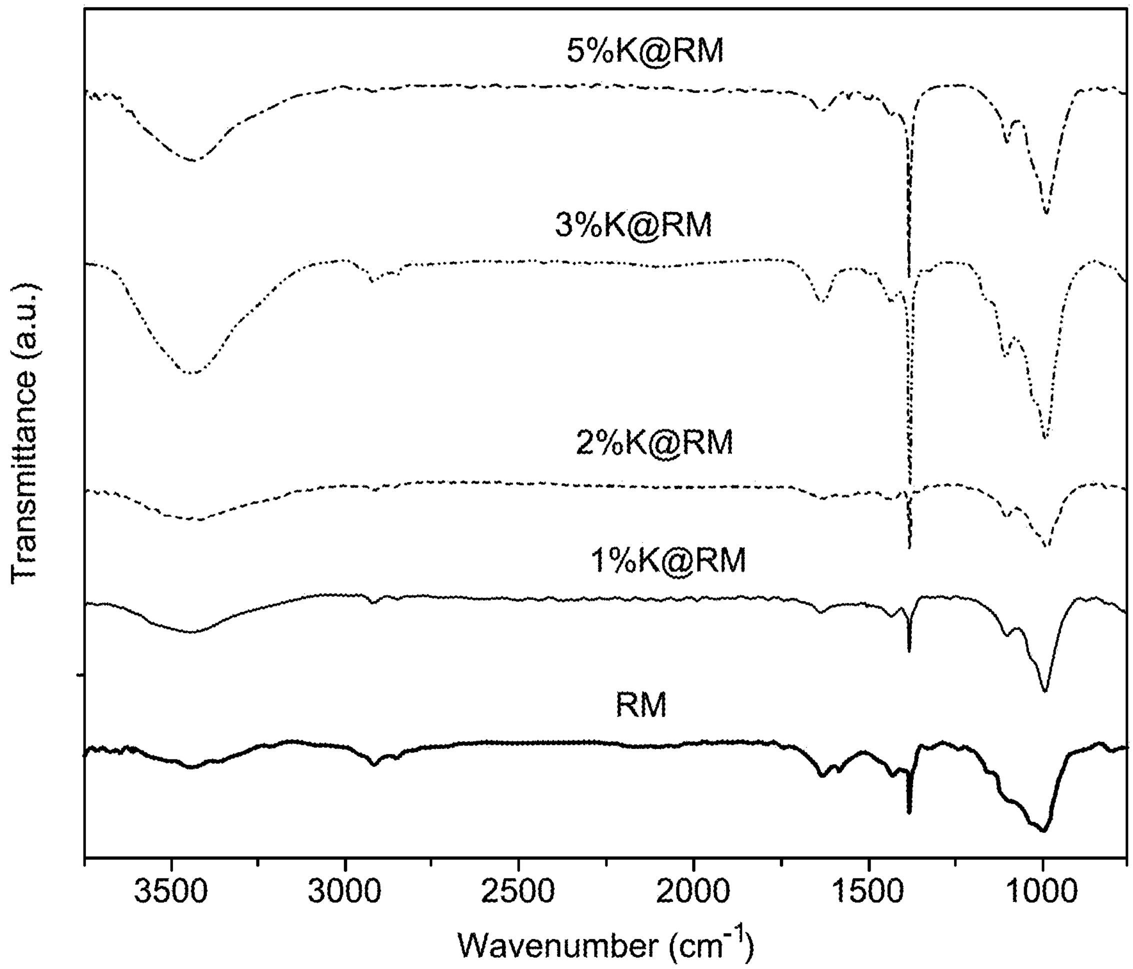
FIG. 3A shows a Fourier transform infrared (FTIR) spectra of K@RM, according to certain embodiments.
Figure 3B:
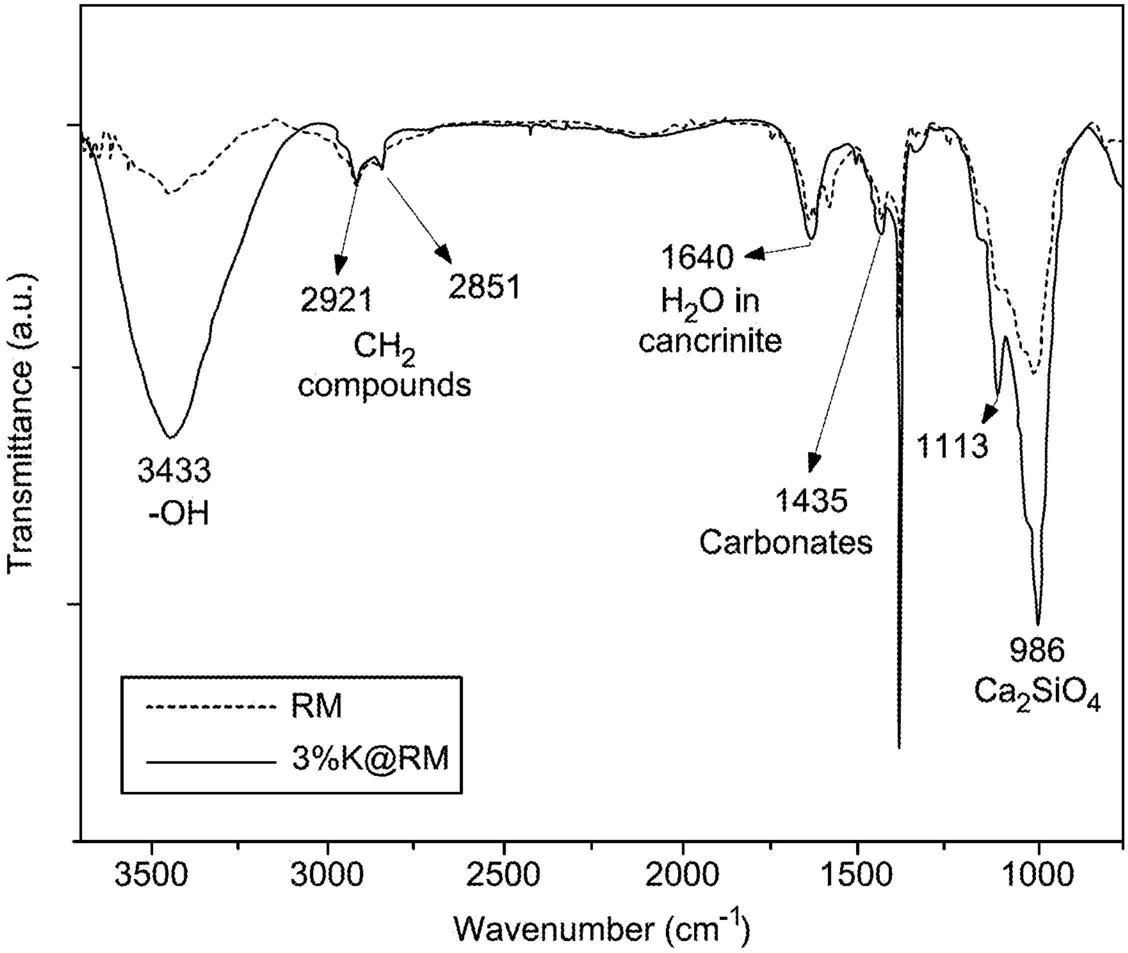
FIG. 3B shows a FTIR spectra for pure RM versus 3% K@RM, according to certain embodiments.

The peak at 19° for AI in RM showed a shift to the right by 0.3° with the addition of 5% K. The observed shift was attributed to crystal lattice strain or lattice deformation, which resulted in smaller grain sizes, as evident from the HR-TEM analysis of 5% K@RM. However, the excess amount of 5% K incorporates higher basicity, which breaks down larger crystals as supported by TEM data [Ribeiro, D. V., et. al., Materials Research, 14, 60-66, 2011, incorporated herein by reference in its entirety]. Further, different 3 wt. % metal ions (X=Na, M g, Cs, Ba, and Sr) were loaded onto the RM in addition to K, and XRD signatures for altered metal ions were evaluated, as shown in FIG. 2B. The clear diffraction peaks corresponding to each individual metal ion were detected in the XRD patterns, as shown in FIG. 2B. The obtained peaks were symbolized for clarity. Furthermore, the FT-IR spectra of pure RM and K-promoted RM with comparable transmission bands, shown in FIGS. 3A-4C and the dominant bands are listed in Table 1. No noticeable change in the absorption band was observed when the concentration of K is increased from 1% to 5%, as shown in FIG. 3A. However, a broad peak at 3433 $cm^{-1}$ appeared, corresponding to the stretching vibrations of (—OH) groups, which was attributed to adsorbed water molecules on the surface or the envelope formed by hydrogen-bonded surface (—OH) groups. The observation was evident when the data for pure RM and 3% K@RM were compared, as shown in FIG. 3B.

Additionally, the peak at 1435 $cm^{-1}$ was indicative of carbonate (calcite), and the peak at 1113 $cm^{-1}$ suggested asymmetric stretching of Si—O—Al framework in cancrinite and hibschite, as well as O—Fe—O in goethite. Furthermore, the peak at 986 $cm^{-1}$signifies Si—O—Si(Al) bonds, corresponding to the anti-symmetric stretching vibrations ($\upsilon_3$) in $SiO_4$ tetrahedra of $Ca_2SiO_4$.

Figure 3C:
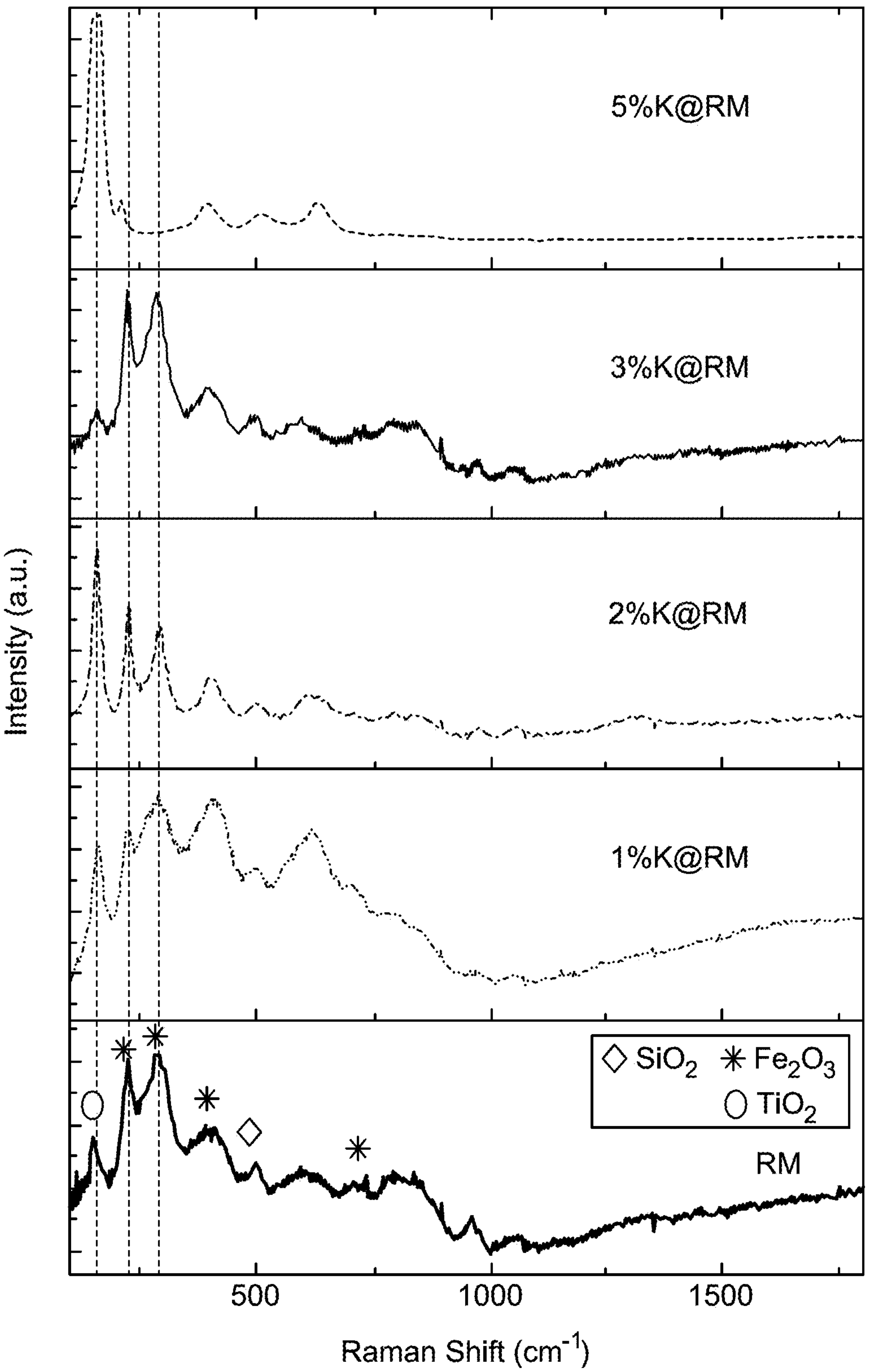
FIG. 3C shows Raman spectroscopy results of K@RM, according to certain embodiments.

The presence of metal-oxides were further confirmed by Raman spectroscopy, as shown in FIG. 3C. The distinct Raman peaks at specific wavelengths in the analysis represent various metal oxides in RM. For example, five prominent peaks at 145 $cm^{-1}$, 211 $cm^{-1}$, 275 $cm^{-1}$, 387 $cm^{-1}$, and 620 $cm^{-1}$, were associated with hematite ($Fe_2O_3$), which is one of the major components in RM. Additionally, the peaks at 145 $cm^{-1}$ and 508 $cm^{-1}$may be attributed to the presence of anatase ($TiO_2$) and quartz ($SiO_2$), respectively [Palmer, S. J. & Frost, R. L., J M ater Sci, 44, 55-63, 2009, incorporated herein by reference in its entirety]. The presence of $Fe_2O_3$ was more noticeable when 3% K was added to RM.

TABLE 1

Functional Groups present in RM calcined at 500° C. for 5 h determined by FTIR measurement.

| Wavenumbers ($cm^{-1}$) | Phases |
|---|---|
| 3433 | OH group, H-bond |
| 1640 | $H_2O$ in Cancrinite |
| 1435 | Carbonate |
| 1113 | Cancrinite, Hibschite, Goethite |
| 986 | $Ca_2SiO_4$ |

Figure 4A:
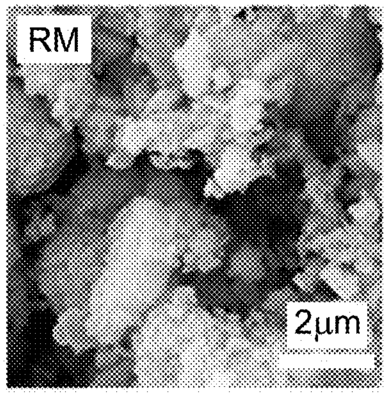
FIG. 4A shows a scanning electron microscope (SEM) image of pure RM at a magnification of 2 micrometer (μm), according to certain embodiments.
Figure 4B:
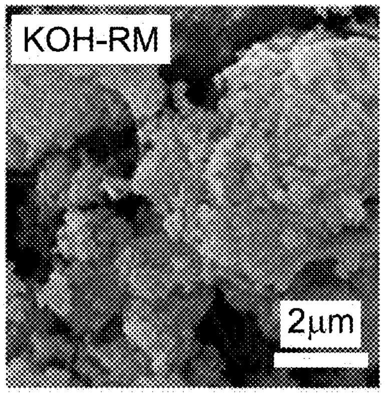
FIG. 4B shows a SEM image of potassium hydroxide (KOH) treated RM (KOH-RM) at a magnification of 2 μm, according to certain embodiments.
Figure 4C:
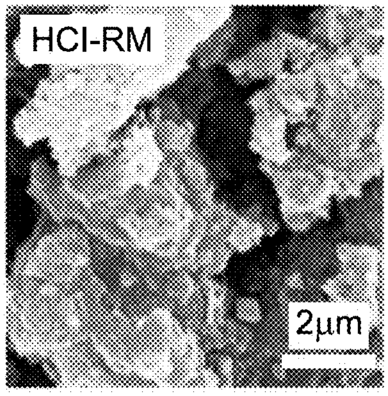
FIG. 4C shows a SEM image of hydrochloric acid (HCl) treated RM (HCL-RM) at a magnification of 2 μm, according to certain embodiments.
Figure 4D:
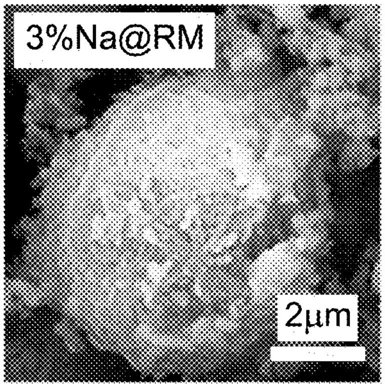
FIG. 4D shows a SEM image of 3 wt. % Na-promoted RM (3% Na@RM) at a magnification of 2 μm, according to certain embodiments.
Figure 4E:
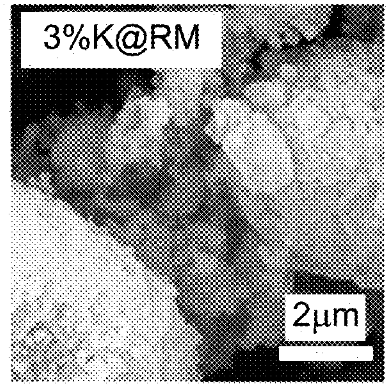
FIG. 4E shows a SEM image of 3% K@RM at a magnification of 2 μm, according to certain embodiments.
Figure 4F:
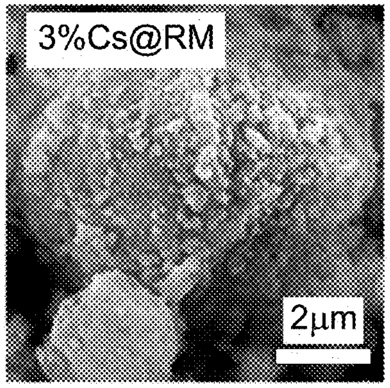
FIG. 4F shows a SEM image 3 wt. % Cs-promoted RM (3% Cs@RM) at a magnification scale of 2 μm, according to certain embodiments.
Figure 4G:
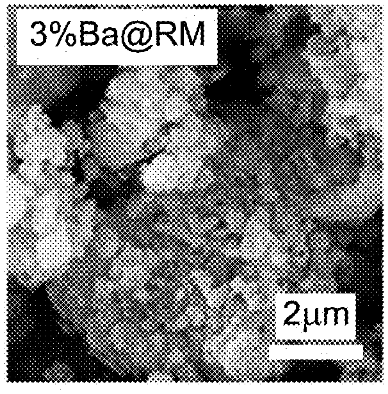
FIG. 4G shows a SEM image of 3 wt % Ba-promoted RM (3Ba@RM) at a magnification of 2 μm, according to certain embodiments.
Figure 4H:
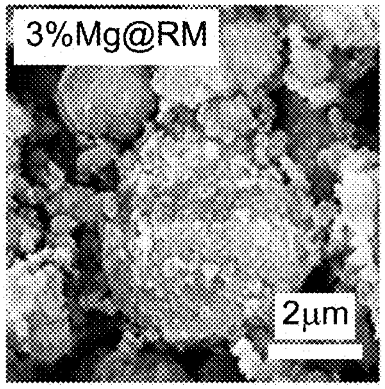
FIG. 4H shows a SEM image of 3 wt % M g-promoted RM (3% M g@RM) at a magnification of 2 μm, according to certain embodiments.
Figure 4I:
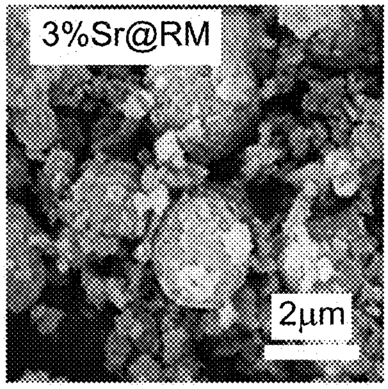
FIG. 4I shows a SEM image of 3 wt % Sr-promoted RM (3% Sr@RM) at a magnification scale of 2 μm, according to certain embodiments.
Figure 4J:
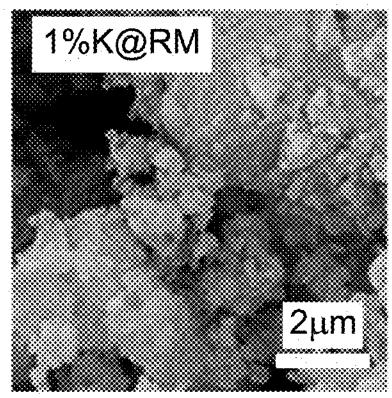
FIG. 4J shows a SEM image of 1 wt % K-promoted RM (1% K@RM) at a magnification of 2 μm, according to certain embodiments.
Figure 4K:
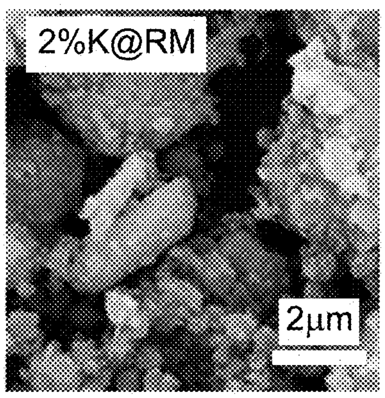
FIG. 4K shows a SEM image of 2 wt % K-promoted RM (2% K@RM) at a magnification of 2 μm, according to certain embodiments.
Figure 4L:
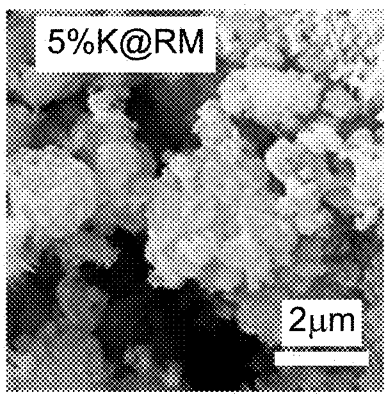
FIG. 4L shows a SEM image of 5 wt % K-promoted RM (5% K@RM) at a magnification of 2 μm, according to certain embodiments.
Figure 5A:
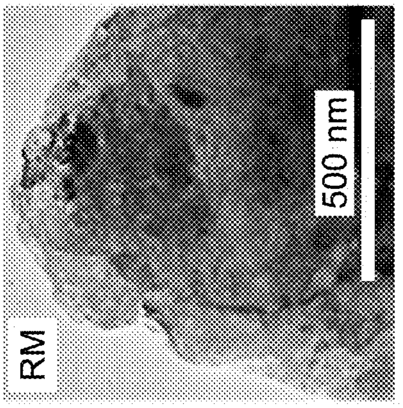
FIG. 5A shows a transmission electron microscopy (TEM) image of pure RM at a magnification of 500 nanometer (nm), according to certain embodiments.
Figure 5B:
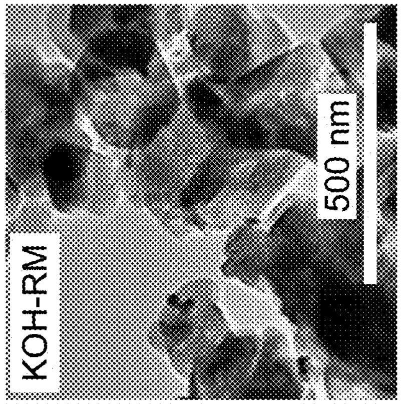
FIG. 5B shows a TEM image of KOH-RM, at a magnification of 500 nm, according to certain embodiments.
Figure 5C:
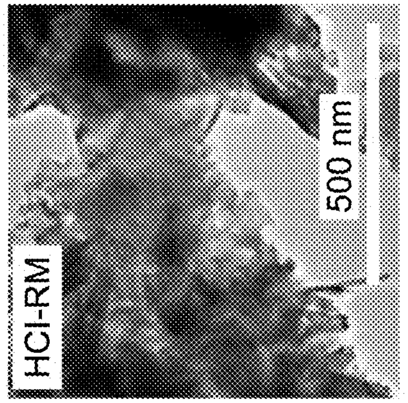
FIG. 5C shows a TEM image of HCL-RM, at a magnification of 500 nm, according to certain embodiments.
Figure 5D:
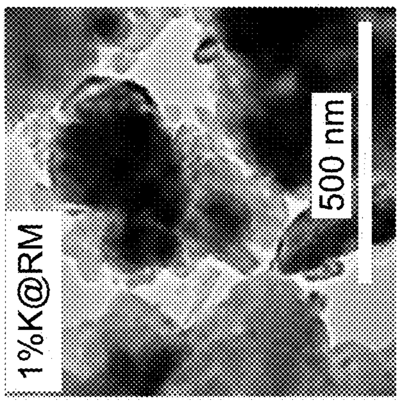
FIG. 5D shows a TEM image of 1% K@RM, at a magnification of 500 nm, according to certain embodiments.
Figure 5E:
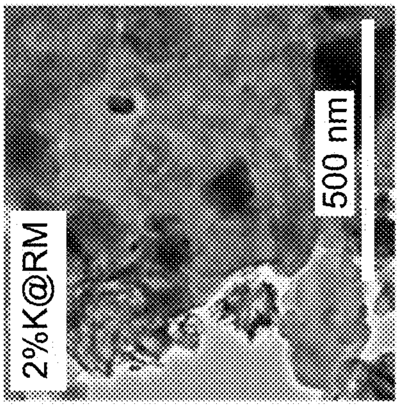
FIG. 5E shows a TEM image of 2% K@RM, at a magnification of 500 nm, according to certain embodiments.
Figure 5F:
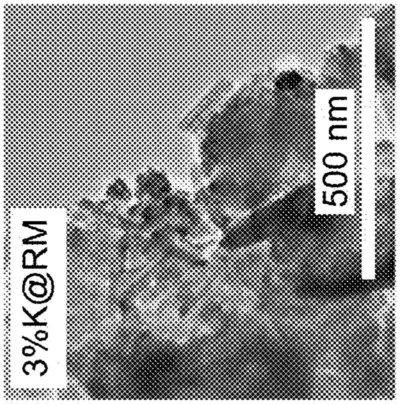
FIG. 5F shows a TEM image of 3% K@RM, at a magnification of 500 nm, according to certain embodiments.
Figure 5G:
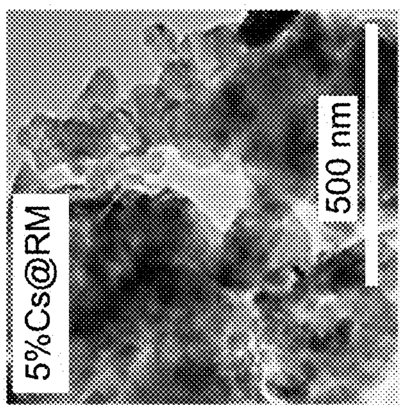
FIG. 5G shows a TEM image of 5% K@RM, at a magnification of 500 nm, according to certain embodiments.
Figure 5H:
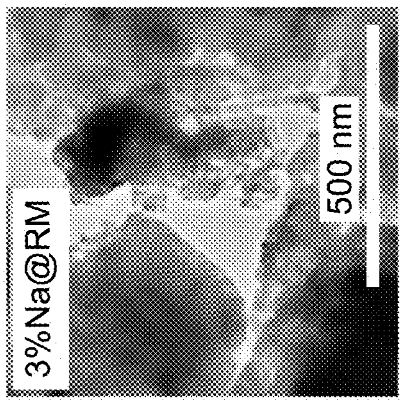
FIG. 5H shows a TEM image of 3% Na@RM, at a magnification of 500 nm, according to certain embodiments.
Figure 5I:
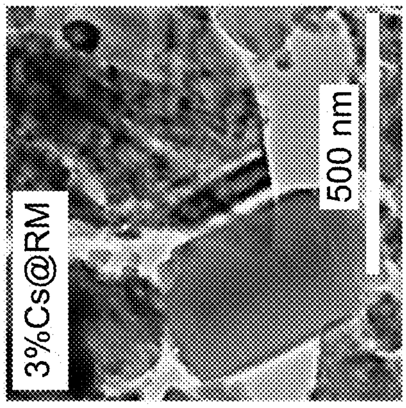
FIG. 5I shows a TEM image of 3% Cs@RM, at a magnification of 500 nm, according to certain embodiments.
Figure 5J:
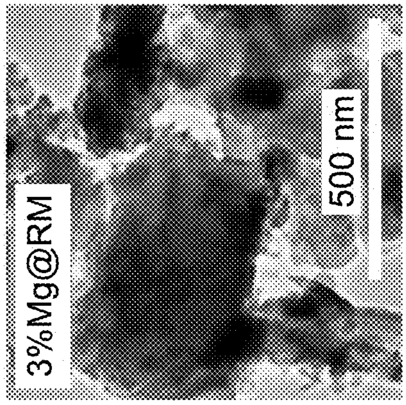
FIG. 5J shows a TEM image of 3% M g@RM, at a magnification of 500 nm, according to certain embodiments.
Figure 5K:
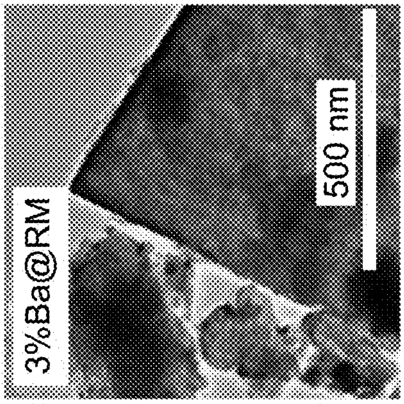
FIG. 5K shows a TEM image of 3% Ba@RM, at a magnification of 500 nm, according to certain embodiments.
Figure 5L:
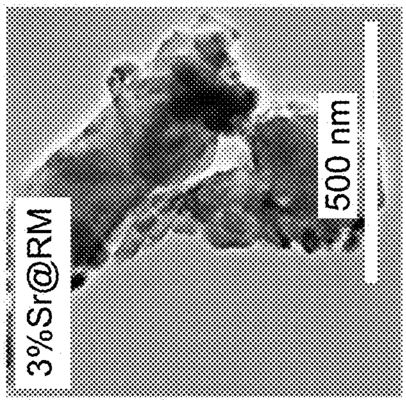
FIG. 5L shows a TEM image of 3% Sr@RM, at a magnification of 500 nm, according to certain embodiments.
Figure 6A:
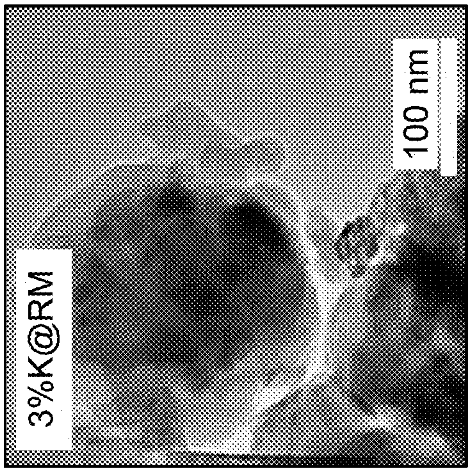
FIG. 6A shows a TEM image of 3% K@RM, at a magnification of 100 nm, according to certain embodiments.
Figure 6B:
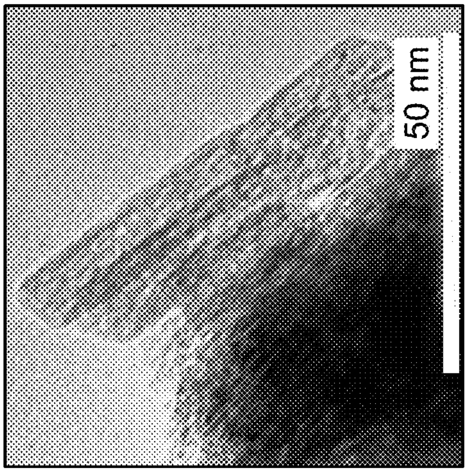
FIG. 6B shows a TEM image of 3% K@RM, at a magnification of 50 nm, according to certain embodiments.
Figure 6C:
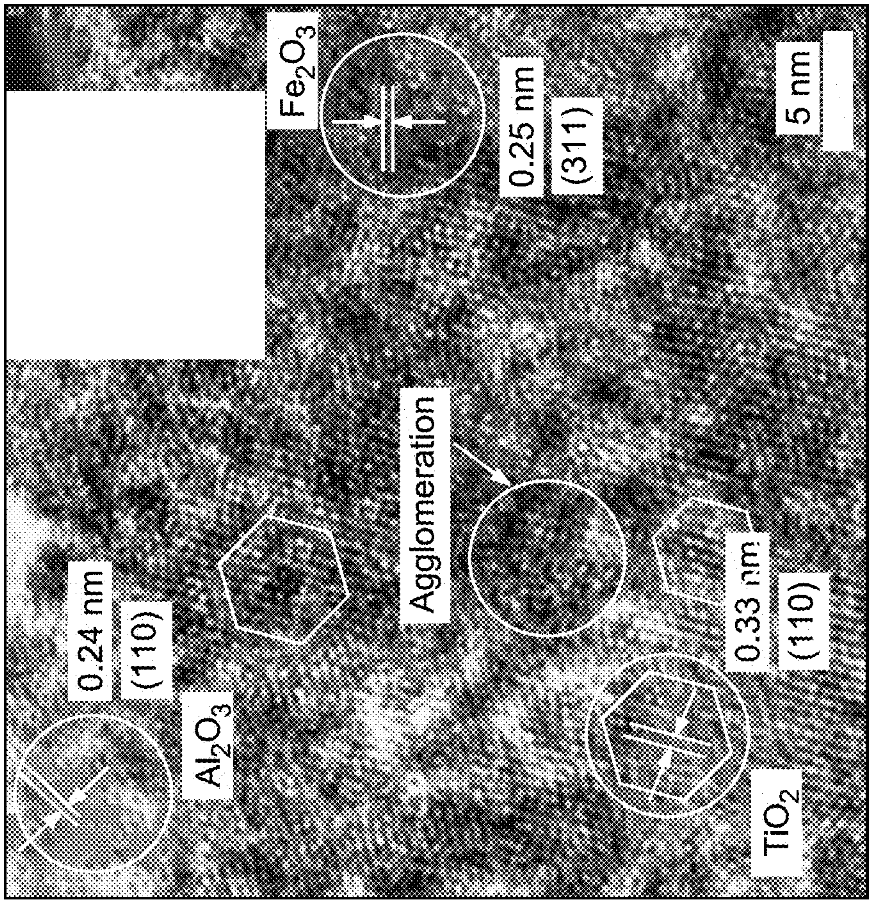
FIG. 6C shows a high-resolution transmission electron microscope (HRTEM) image of 3% K@RM, according to certain embodiments.
Figure 6D:
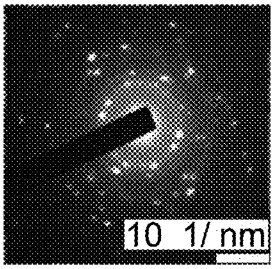
FIG. 6D shows a selected area electron diffraction (SAED) pattern of the 3% K@RM shown in FIG. 6C, according to certain embodiments.

Further, SEM was conducted to evaluate the surface morphology of pure RM and alkali-metal-promoted RM catalysts, as shown in FIGS. 4A-4L. The heterogeneous internal structure of RM was confirmed through SEM imaging of pure RM, revealing particles and crystals of various sizes and morphologies, ranging from nanometers to micrometers. The structures were formed through agglomeration, as shown in FIGS. 4A-4L. The higher agglomeration of particles was observed with the KOH-treated samples, thereby decreasing the surface area and leading to the loss of active sites. Furthermore, SEM evaluations revealed that monovalent Na, K, and Cs metal-promoted RM exhibited a noticeable increase in particle size compared to divalent Mg, Ba, and Sr metal-promoted RM, with a fixed metal ion concentration of 3%, as shown in FIGS. 4D-4I. The observations revealed no significant changes in morphology when the potassium content was increased from 1% to 3%, as shown in FIGS. 4J-4L. However, a higher amount of 5% K into the RM may promote further agglomeration, which diminishes the catalytic activity. EDS attached to SEM was performed and confirmed the presence of the constituent elements of RM and corresponding dopant elements.

The TEM analysis depicted in FIGS. 5A-5L show that the particles present in RM and RM-based catalysts exhibit diverse sizes and shapes, with different crystal plane orientations due to the presence of various metal nanocrystals. KOH-treated RM showed irregularly shaped smaller particles, whereas HCl-treated RM revealed longer arrays of crystal planes, resulting in $TiO_2$ rod-like structures [Dai, S., et al., Nanoscale Res Lett, 5, 1829-1835, 2010]. The introduction of K had an impact on the grain size and crystallinity of the constituent materials. Pure RM crystallinity was enhanced by a slight addition of K. The trend leveled off to 3 wt. % of K. However, the higher amount of 5% K in RM starts to break the long-range order of the lattice, causing smaller grains and a large amount of grain boundary. However, no significant changes in the morphology of the particles were observed. K-promoted RM resulted in the formation of particles with pores and rod-like structures, attributed to the contribution of quartz and rutile in RM. The unidirectional crystal growth, which provides the tubular shape, comes from the combined effect of AI substitution on hematite [Dilorio, E., et al. Geochim Cosmochim Acta, 237, 155-170, 2018, incorporated herein by reference in its entirety]. The effect of Na, Cs, Mg, and Sr on RM particle shape and size showed a similar effect. However, 3% Ba@RM produced larger cubic particles due to the cubic nature of BaO.

The HR-TEM analysis depicted slip, dislocation, and planar defect on the structure, as shown in FIGS. 6A-6D. HR-TEM of 3% K@RM revealed clear and bright surface of the particle. According to previous observations, RM is a complex mixture of different metal oxides and the HRTEM image clearly established the presence of $Al_2O_3$ with $d_{(110)}$=spacing 0.24 nm, hematite $Fe_2O_3$ with $d_{(311)}$=0.25 nm. In addition, the presence of hexagonal anatase $TiO_2$ nanoparticles with $d_{(101)}$=0.35 nm and rutile phase $TiO_2$ nanorods with $d_{(110)}$=0.33 nm was confirmed by the matching of inter-planar distance (d) [Dai, S., et. al., Nanoscale Res Lett, 5, 1829-1835, 2010; Gong, W., et. al., Materials, 10, 1192, 2017; and Thomas, P., et. al., J Appl Phys, 117, 2015, each of which is incorporated herein by reference in its entirety].

Example 8: Catalytic Characterization

Figure 7A:
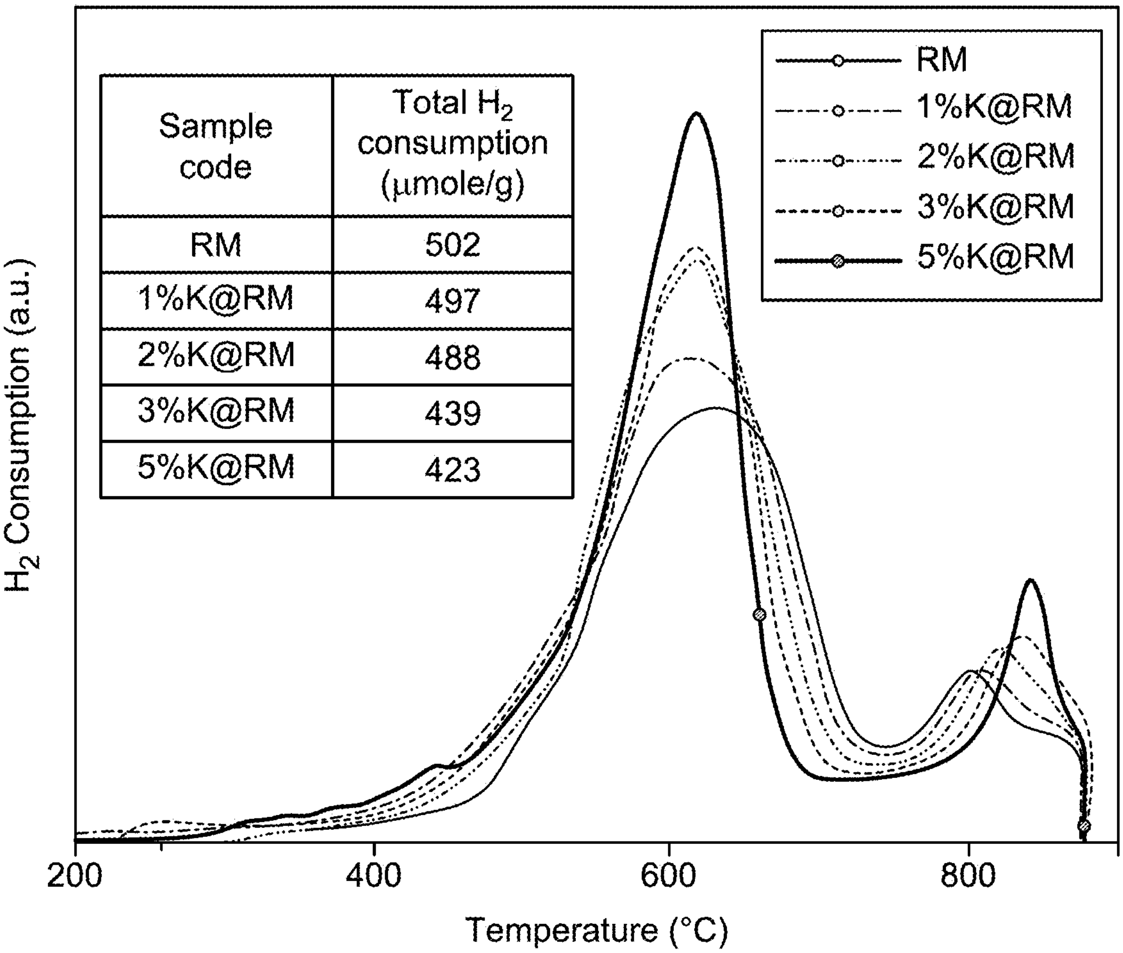
FIG. 7A is a graph of hydrogen temperature-programmed reduction ($H_2$-TPR) profile of 1% K@RM, 2% K@RM, 3% K@RM, and 5% K@RM, according to certain embodiments.

The hydrogen consumption ability of pure and modified RM samples was assessed using $H_2$-TPR, with the spectra shown in FIG. 7A. A well-defined reduction peak at 502° C. for the pure RM was observed, as shown in FIG. 7A. In general, hematite ($\alpha$-$Fe_2O_3$) is reduced by $H_2$ in the range of 220° C. to 680° C., while magnetite reduces in the range of 600° C. to 800° C. [Pineau, A., et. al., Thermochim Acta, 447, 89-100, 2006; and Li, P., et. al., Int J Hydrogen Energy, 47, 31140-31151, 2022, each of which is incorporated herein by reference in its entirety]. The other metals that were available in the RM sample such as K, Mg, N a, P, and S were reduced in the range of 250° C. to 850° C. The broad peak is composed of overlapping peaks from each of these constituent elements. However, modifying the RM sample with different concentrations of potassium led to a reduction in $H_2$ consumption, as shown in FIG. 7A. The observed total $H_2$ consumption for the parent RM sample was 502 micromoles per gram (μmol/g) at temperatures ranging from 200° C. to 850° C. A s the concentration of K increased to 5 wt. %, a reduction in $H_2$ consumption from 502 μmol/g to 423 μmol/g was seen. In addition, it was observed that the first peak, which was centered around 600° C., shifted to a lower temperature as the concentration of K was increased in the sample. On the other hand, the second peak located after 800° C. was shifted towards higher temperatures which confirmed the contribution of K in changing the elemental phase of the RM.

Figure 7B:
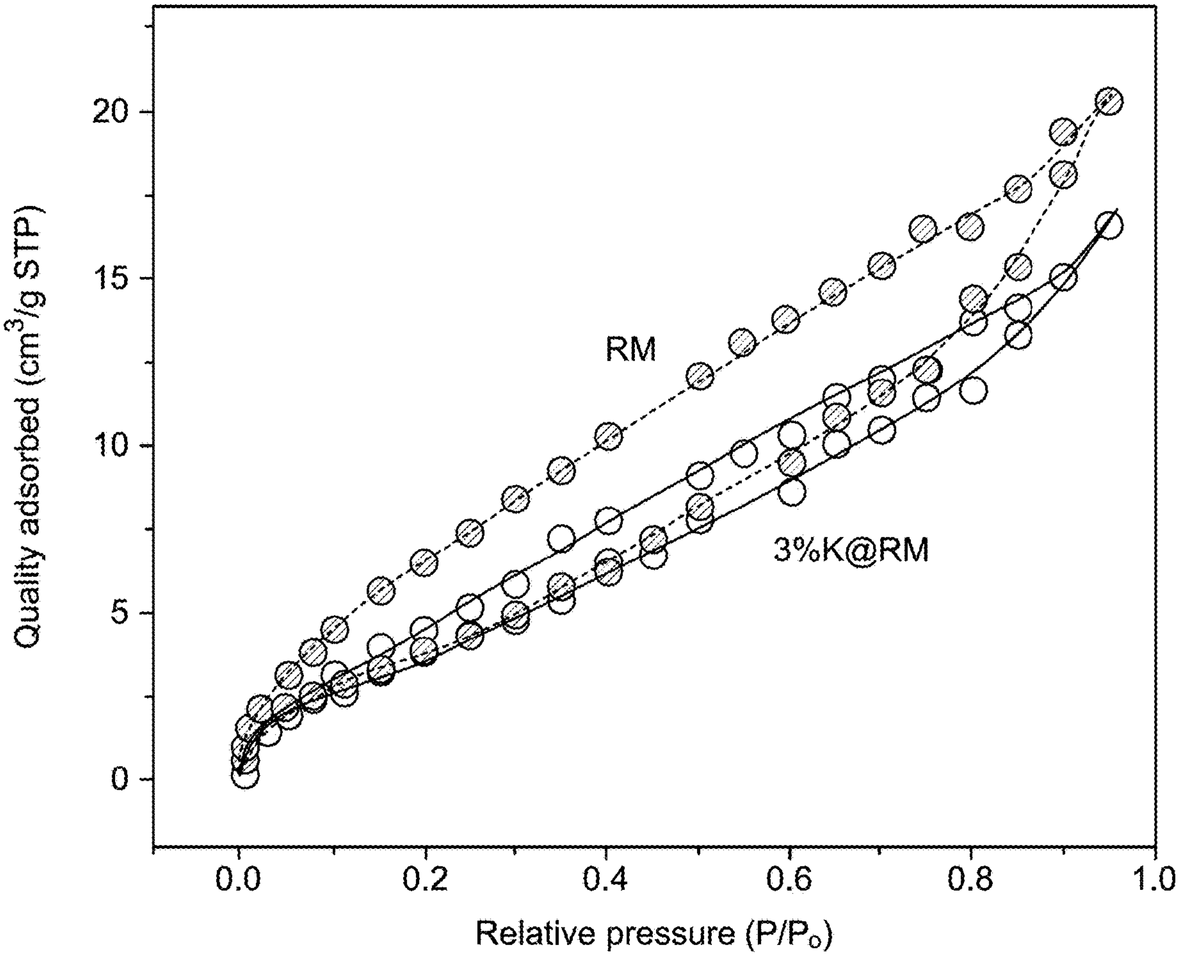
FIG. 7B depicts a graph of Brunauer-Emmett-Teller (BET) isotherms of RM samples and 3% K@RM samples, according to certain embodiments.

The textural properties of pure RM and 3% alkali metal-loaded RM catalysts are shown in FIG. 7B. In the RM curve, the evident adsorption and desorption curves diverged as the relative pressure increased, as shown in FIG. 7B. A substantial hysteresis loop was observed between relative pressures of >0 and 1.0, indicating the presence of huge mesoporosity in the prepared catalysts. According to IU PAC isotherm data, type IV suggests the presence of numerous mesopores and macropores in RM with monolayer and multilayer adsorption [Abebe, B., et. al., Journal of Encapsulation and Adsorption Sciences, 08, 225-255, 2018, incorporated herein by reference in its entirety]. In contrast, the 3% K@RM hysteresis loop demonstrated a significant decrease in adsorption capacity. The relative pressure was below 0.2 bar, and the adsorption and desorption curves were nearly superimposed, indicating the existence of micropores. BET surface area decreased gradually from 20 $m^2$/gm to 11.2 $m^2$/gm as the K loading increased to 5%. The adsorption of gas was facilitated in RM instead of K loaded.

TABLE 2

Pore volume and surface area of pure RM and different percent K-promoted RM obtained from BET measurement.

| Sample | Pore volume (cc/g) | Surface area ($m^2/g$) |
|---|---|---|
| RM | 0.029 | 20.36 |
| 1% K @ RM | 0.026 | 14.19 |
| 3% K @ RM | 0.023 | 15.26 |
| 5% K @ RM | 0.019 | 11.2 |

FIG. BA provides a comparison between the $CO_2$ hydrogenation results over pure RM and alkali metal-promoted catalysts after 6 h under the $CO_2$:$H_2$ (3:1) stream. Over pure RM as a control catalyst, 22% $CO_2$ conversion was achieved with low $C_{2-4}$ olefins selectivity under 30 bar pressure at 375° C. (GHSV of 4500 $mL \cdot g^{-1} \cdot h^{-1}$). Therefore, the results of acid and base-treated RM catalysts were employed for the $CO_2$ hydrogenation. Both RM treated with HCl and KOH produced a 16% conversion of $CO_2$. Although, a 36% of jump in hydrocarbon selectivity was noted with the KOH-treated RM, the olefins selectivity dropped to 1% compared to 12% in the HCl-treated sample. The higher olefins selectivity for HCl-treated RM and their higher DI-water washing caused the removal of smaller metal cations from RM and enhanced the crystallinity of larger cations, which may boost the active sites of RM needed for the $CO_2$ hydrogenation for olefins selectivity.

Figure 8A:
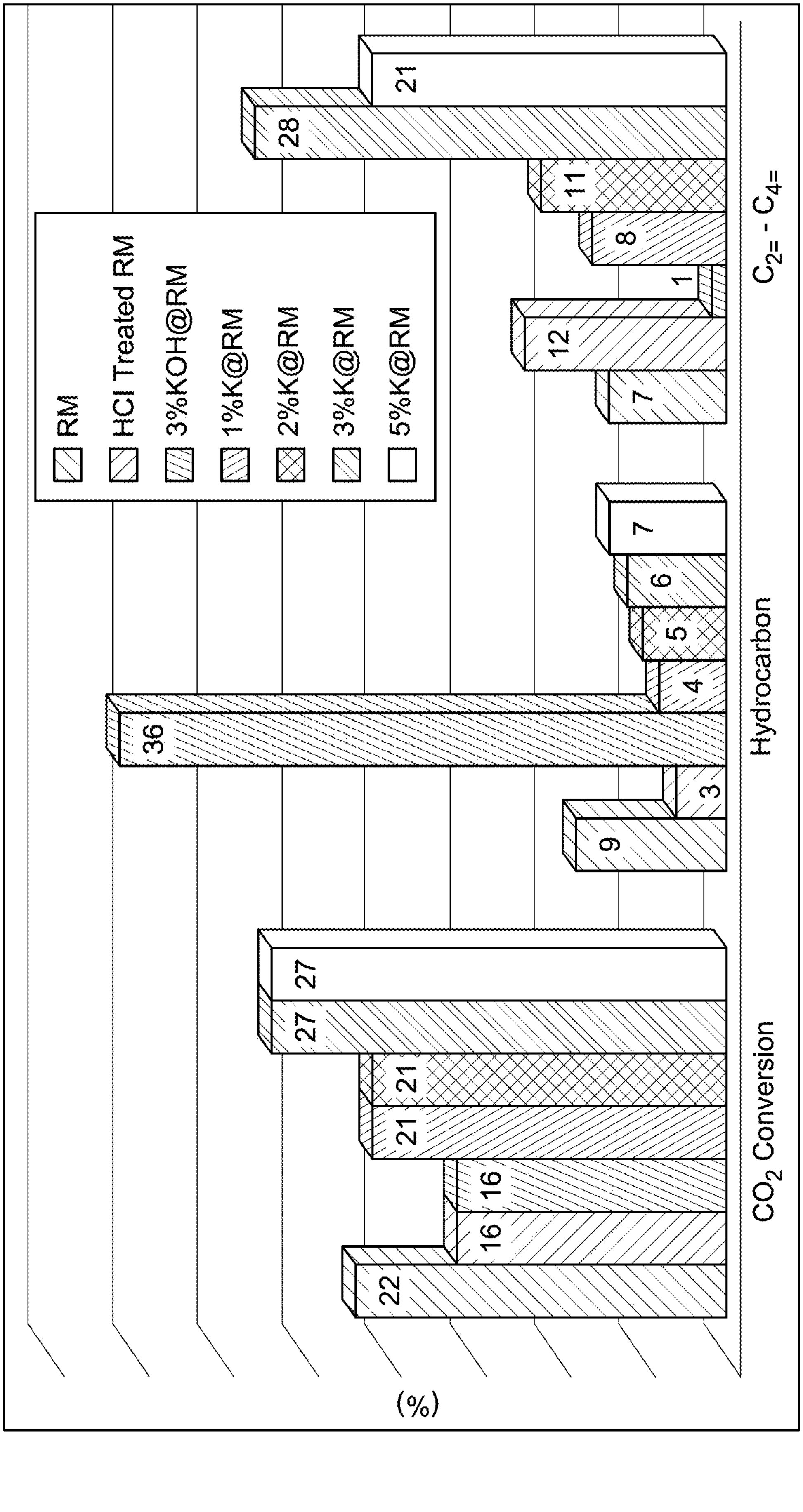
FIG. 8A illustrates a column graph for $CO_2$ conversion and olefins selectivity data of pure RM, HCL-RM, 1% K@RM, 2% K@RM, 3% K@RM, and 5% K@RM, according to certain embodiments.

The effect of varied concentrations of 1 wt %, 2 wt %, 3 wt %, 5 wt % K on $CO_2$ conversion and olefins selectivity is shown in FIG. 8A. The addition of 1% K as a promoter improved the $CO_2$ conversion to 21% selectivity towards olefins. On increasing the K concentration to 3%, the highest 27% conversion of $CO_2$ with 28% olefins ($C_{2-4}$=) selectivity was achieved under the same reaction condition. This effect was attributed to the promotion of $CO_2$ adsorption and suppression of further hydrogenation of produced olefins enhanced the selectivity [Ramirez, A., et al., ACS Catal, 8, 9174-9182, 2018, incorporated herein by reference in its entirety]. The conversion remains unchanged on further loading of K to 5%, however, the olefins selectivity dropped to about 21%. Elevating the K content attenuated the hydrogenation activity of Fe, consequently fostering the propensity for olefin preference formation [Santos, V. P., et al., Nat Commun, 6, 6451, 2015, incorporated herein by reference in its entirety]. This, in turn, may facilitate the re-adsorption of olefins, thereby enabling extended chain growth.

$$Fe_2O_3 + 6HCl \longrightarrow 2FeCl_3 + 3H_2O \quad (4)$$

Figure 8B:
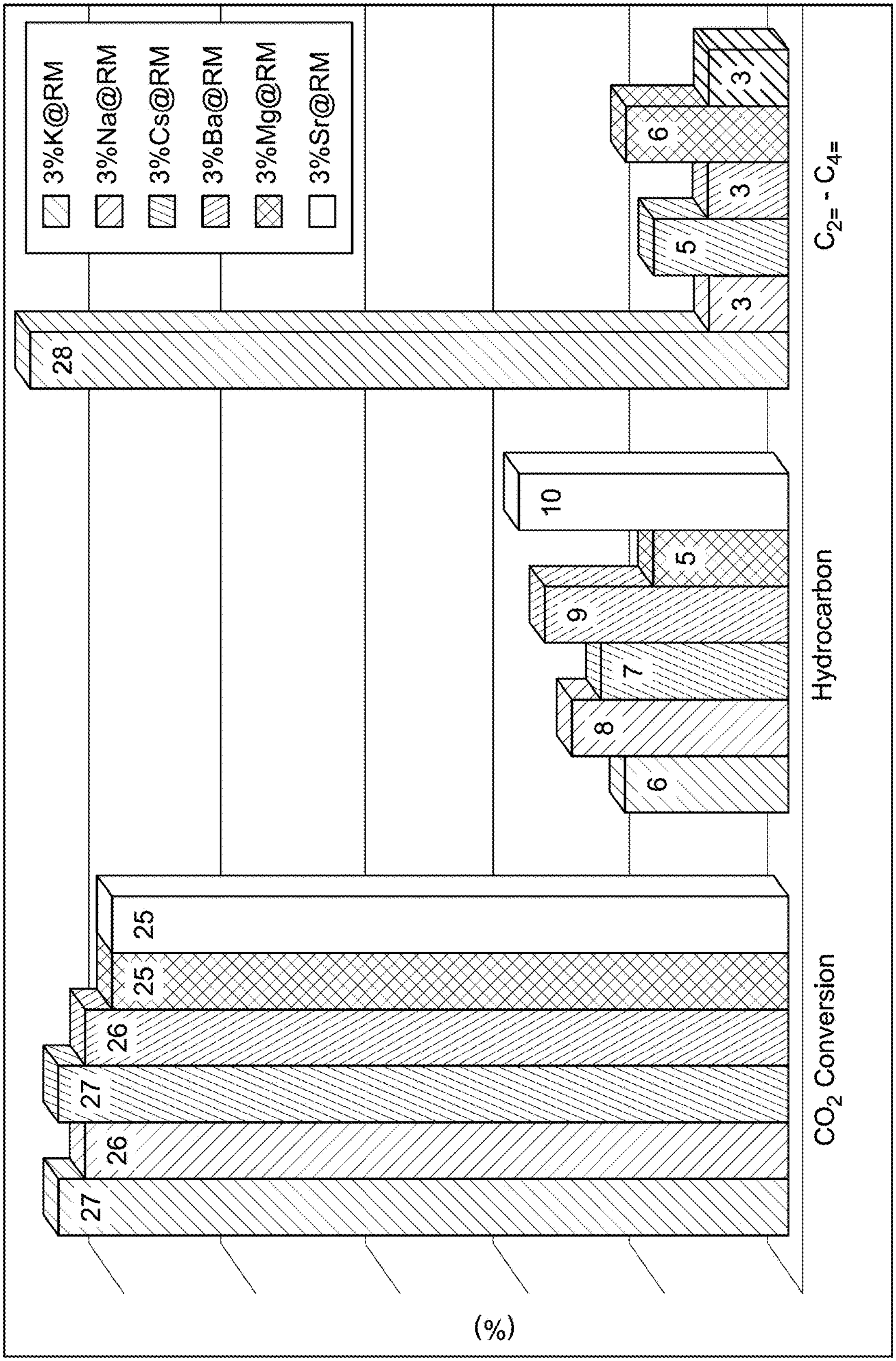
FIG. 8B illustrates a column graph for $CO_2$ conversion and olefins selectivity data of 3% K@RM, 3% Na@RM, 3% Cs@RM, 3% Ba@RM, 3% Mg@RM, and 3% Sr@RM, according to certain embodiments.

A broader scope of the effect of alkali metal promoters on $CO_2$ hydrogenation was evaluated under the optimized reaction condition. A series of alkali metals, including Na, Cs, Ba, M g, and Sr, were employed at a fixed 3% concentration and impregnated into the RM for $CO_2$ hydrogenation. The 3% Na-loaded RM demonstrated a comparable 26% $Co_2$ conversion with a very low olefins selectivity of 3%, as shown in FIG. 8B. However, the Cs promoted RM, retained its reactivity towards the $CO_2$ conversion as 3% K loaded RM. A trend of very low olefins selectivity (3-6%) was established with these alkali metals with the RM.

The aspects of the present disclosure provide the $CO_2$ hydrogenation catalysts including RM, and a method of $CO_2$ hydrogenation using the aforementioned catalyst. In particular, RM was used since the catalytic properties of RM make it a valuable resource for addressing environmental challenges, promoting waste valorization, and advancing green, economically viable technologies. Based on the product selectivity of the catalysts, there is potential to manipulate the reaction to produce other important hydrocarbons. RM-based catalysts, by properly selecting promoter materials, serve as a cost-effective catalyst to overcome the challenges of $CO_2$. RM calcined at 500° C. performed better as compared to HCl and KOH-treated RM. Different metal promoters have shown distinguished effects for $CO_2$ hydrogenation. In particular, a series of metals (M=Na, K, Cs, Ba, M g, and Sr) promoted RM as catalysts were fabricated, characterized, and evaluated for the $CO_2$ hydrogenation to produce olefins. First, Acid and base treated RM using hydrochloric acid (HCl) and potassium hydroxide(KOH), respectively, were prepared, and activity towards $CO_2$ hydrogenation was evaluated. Furthermore, 3% K promoted RM was the best performer with 27% $Co_2$ conversion and 28% olefin selectivity. The source of K was a vital parameter in this regard as 3% K in RM from its $NO_3^-$ and $OH^-$ sources showed different results. The estimation opens a new window for future work to enhance catalytic performance using various sources of the same metal promoter. Furthermore, present disclosure concludes that the weight percentage may be tunable parameter for achieving a targeted amount of olefin products.

Numerous modifications and variations of the present disclosure are possible in light of the above teachings. Therefore, it is to be understood that within the scope of the appended claims, the invention may be practiced other than as specifically described herein.

The invention claimed is:

1. A method of hydrogenating carbon dioxide, the method comprising:

providing a $CO_2$ hydrogenation catalyst comprising an alkali-metal enriched bauxite residue comprising $CaCO_3$, $Fe_2O_3$, FeO(OH), $Al(OH)_3$, sodalite, muscovite, $Na_5Al_2CSi_3O_{15}$, and potassium, wherein the potassium is present in the $CO_2$ hydrogenation catalyst at from 3 wt. % to 5 wt. % potassium based on a total weight of the $CO_2$ hydrogenation catalyst by ICP-OES;

combining particles of the $CO_2$ hydrogenation catalyst and a gaseous mixture of $CO_2$ and $H_2$ in a reactor; and reacting at least a portion of the $CO_2$ and $H_2$ in the gaseous mixture in the presence of the $CO_2$ hydrogenation catalyst at a temperature of 200 to 550° C. to form a hydrocarbon mixture comprising a $C_2$-$C_4$ olefin;

wherein the $CO_2$ hydrogenation catalyst has a surface area of 11 to 16 $m^2/g$;

wherein the $CO_2$ hydrogenation catalyst has a pore volume of 0.015 to 0.025 $cm^3/g$;

wherein the $CO_2$ hydrogenation catalyst has a hydrogen temperature-programmed reduction ($H_2$-TPR) of from 400 to 450 micromoles per gram (mol) at a temperature of 200 to 850° C.;

wherein the method has a $CO_2$ conversion of from 25% to 30% based on a total number of moles of CO, introduced;

and wherein the method has a $C_2$-$C_4$ olefin selectivity of from 20% to 30%.

2. The method of claim 1, wherein the $CO_2$ hydrogenation catalyst further comprises $Al_2O_3$ and $TiO_2$.

3. The method of claim 2, wherein the $TiO_2$ is rutile and the $Fe_2O_3$ is $\alpha$-$Fe_2O_3$.

4. The method of claim 1, wherein the $CO_2$ hydrogenation catalyst further comprises AlO(OH).

5. The method of claim 1, wherein the $CO_2$ hydrogenation catalyst has a mean particle size of 0.1 to 10 μm.

6. The method of claim 1, further comprising forming the $CO_2$ hydrogenation catalyst by:

calcining red mud at 300 to 700° C. for 1 to 12 hours to produce a calcined red mud;

treating the calcined red mud with a concentrated acid to produce an acid-treated red mud;

grinding the acid-treated red mud with a potassium source to form a precursor mixture; and calcining the precursor mixture at 300 to 700° C. for 1 to 12 hours to produce the $CO_2$ hydrogenation catalyst.

7. The method of claim 6, wherein the potassium source comprises potassium nitrate.

8. The method of claim 6, wherein the potassium source does not comprise potassium hydroxide.

9. The method of claim 6, wherein the concentrated acid is HCl having a concentration of 30% to 38% by weight in water.

10. The method of claim 1, wherein the gaseous mixture has a volume ratio of the $CO_2$ to the $H_2$ of 1:10 to 10:1.

11. The method of claim 10, wherein the gaseous mixture has a volume ratio of the $CO_2$ to the $H_2$ of 1:1 to 5:1.

12. The method of claim 1, wherein the reacting is performed at a pressure of from 5 to 100 bar.

13. The method of claim 8, further comprising activating the $CO_2$ hydrogenation catalyst by drying the $CO_2$ hydrogenation catalyst by heating to 400 to 600° C. under flowing nitrogen, and reducing the $CO_2$ hydrogenation catalyst by heating to 400 to 600° C. in the presence of a reducing gas mixture comprising hydrogen and substantially free of $CO_2$; wherein the hydration catalyst is activated prior to combining particles of the $CO_2$ hydrogenation catalyst and the gaseous mixture of $CO_2$ and $H_2$ in the reactor.

* * * * *